United States Patent
Lesuisse et al.

(10) Patent No.: US 7,019,011 B2
(45) Date of Patent: *Mar. 28, 2006

(54) AMINOINDAZOLE DERIVATIVES AS MEDICAMENTS AND PHARMACEUTICAL COMPOSITIONS INCLUDING THEM

(75) Inventors: Dominique Lesuisse, Montreuil (FR); Gilles Dutruc-Rosset, Paris (FR); Franck Halley, Sevres (FR); Didier Babin, Montigny (FR); Thomas Rooney, Orsay (FR); Gilles Tiraboschi, Chevilly Larue (FR)

(73) Assignee: Aventis Pharma S.A., Antony (FR)

( * ) Notice: Subject to any disclaimer, the term of this patent is extended or adjusted under 35 U.S.C. 154(b) by 76 days.

This patent is subject to a terminal disclaimer.

(21) Appl. No.: 10/654,698

(22) Filed: Sep. 4, 2003

(65) Prior Publication Data

US 2004/0132794 A1 Jul. 8, 2004

Related U.S. Application Data

(60) Provisional application No. 60/444,630, filed on Feb. 4, 2003.

(30) Foreign Application Priority Data

Dec. 12, 2002 (FR) .................................. 02 15720

(51) Int. Cl.
 *C07D 231/56* (2006.01)
 *C07D 241/10* (2006.01)
 *A61K 31/416* (2006.01)

(52) U.S. Cl. ................... 514/266.2; 514/315; 514/403; 514/405; 514/407; 544/116; 544/371; 546/199; 546/275.7; 548/348.1; 548/362.1

(58) Field of Classification Search ............ 548/362.1; 514/403, 407, 405, 315, 266.2; 544/116, 544/371; 546/199, 275.7
See application file for complete search history.

(56) References Cited

FOREIGN PATENT DOCUMENTS

WO WO 02/22601 A1 3/2002
WO WO 03/028720 A1 4/2003

OTHER PUBLICATIONS

U.S. Appl. No. 10/654,703.*
U.S. Appl. No. 10/385,871.*

* cited by examiner

*Primary Examiner*—Joseph K. McKane
*Assistant Examiner*—Susannah E. Lee
(74) *Attorney, Agent, or Firm*—Irving Newman

(57) ABSTRACT

The present invention relates to novel derivatives of general formula (I)

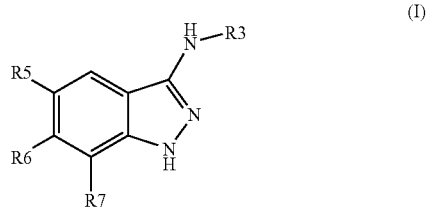

in which
R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, COOR1, SO$_2$R1, C(=NH)R1 or C(=NH)NR1 radical;
R5, R6 and R7 are, independently of one another, chosen from the following radicals: halogen, CN, NO$_2$, NH$_2$, OH, OR8, COOH, C(O)OR8, —O—C(O)R8, NR8R9, NHC(O)R8, C(O)NR8R9, NHC(S)R8, C(S)NR8R9, SR8, S(O)R8, SO$_2$R8, NHSO$_2$R8, SO$_2$NR8R9, —O—SO$_2$R8, —SO$_2$—O—R8, trifluoromethyl, trifluoromethoxy, (1–6C)alkyl, (1–6C)alkoxy, aryl, aryl (1–6C)alkyl, heteroaryl, heteroaryl(1–6C)alkyl, heterocycle, cycloalkyl, alkenyl, alkynyl, adamantyl or polycycloalkyl.

8 Claims, No Drawings

AMINOINDAZOLE DERIVATIVES AS MEDICAMENTS AND PHARMACEUTICAL COMPOSITIONS INCLUDING THEM

This application claims the benefit of Provisional Application No. 60/444,630, filed Feb. 4, 2003.

The present invention relates to the use of derivatives of formula (I):

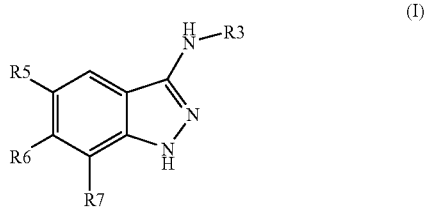

or their pharmaceutically acceptable salts as kinase inhibitor.

The subject matter of the invention is the use of the aminoindazole derivatives of formula (I) and their pharmaceutically acceptable salts in the preparation of pharmaceutical compositions intended to prevent and treat diseases which can result from an abnormal activity of kinases, such as, for example, those involved in neurodegenerative diseases, Alzheimer's disease, Parkinson's disease, frontoparietal dementia, corticobasal degeneration, Pick's disease, strokes, cranial and spinal traumas and peripheral neuropathies, obesity, metabolic diseases, type II diabetes, essential hypertension, atherosclerotic cardiovascular diseases, polycystic ovaries syndrome, syndrome X, immunodeficiency and cancer, the pharmaceutical compositions comprising the novel aminoindazole derivatives and their pharmaceutically acceptable salts and the novel aminoindazole derivatives and their pharmaceutically acceptable salts.

Patent application WO 02/074388 describes aminoindazole derivatives of type (a) that are potassium-channel activators

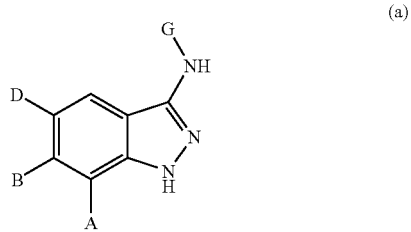

in which G is

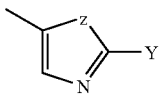 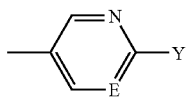

Z is NX0, S or O
E is N or CX1
Y is halogen, X2 or OX2
X0, X1 and X2 are halogen, alkyl or a substituted alkyl
A, B and D are hydrogen, halogen, substituted or unsubstituted alkyl, C(O)pR13, C(O)NR13R14, SO2NR13, R14, S(O)pR15, OR15 or NR13R14 p is an integer from 0 to 2

R13 and R14 are hydrogen, substituted or unsubstituted alkyl, substituted or unsubstituted cycloalkyl, substituted or unsubstituted heteroaryl, substituted or unsubstituted heterocycle, substituted or unsubstituted heteroalkyl, substituted or unsubstituted heteroaryl-heteroalkyl, or substituted or unsubstituted aryl-heteroalkyl R15 is substituted or unsubstituted alkyl, substituted or unsubstituted cycloalkyl, substituted or unsubsubstituted heteroaryl, substituted or unsubstituted heterocycle, substituted or unsubstituted heteroalkyl, substituted or unsubstituted heteroaryl-heteroalkyl, or substituted or unsubstituted aryl-heteroalkyl.

The present invention relates to derivatives of formula (I) in which:

R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1, C(=NH)R1 or C(=NH)NR1 radical; these radicals optionally being substituted by 1 or more substituents chosen from halogen, CN, NO$_2$, NH$_2$, OH, OR1, COOH, C(O)OR1, —O—C(O)R1, NR1R2, NHC (O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, heterocycle, formyl, trifluoromethyl, trifluoromethylsulfanyl, trifluoromethoxy or (1–6C)alkyl;

R5, R6 and R7 are, independently of one another, chosen from the following radicals halogen, CN, NO2, NH$_2$, OH, COOH, C(O)OR8, —O—C(O)R8, NR8R9, NHC(O)R8, C(O)NR8R9, NHC(S)R8, C(S)NR8R9, SR8, S(O)R8, SO$_2$R8, NHSO$_2$R8, SO$_2$NR8R9, —O—SO$_2$R8, —SO$_2$—O—R8, trifluoromethyl, trifluoromethoxy, (1–6C)alkyl, (1–6C)alkoxy, aryl, aryl(1–6C)alkyl, heteroaryl, heteroaryl (1–6C)alkyl, heterocycle, cycloalkyl, alkenyl, alkynyl, adamantyl or polycycloalkyl; these radicals optionally being substituted by 1 or more substituents chosen from halogen, CN, NO$_2$, NH$_2$, OH, OR10, COOH, C(O)OR10, —O—C (O)R10, NR10R11, NHC(O)R10, C(O)NR10R11, NHC(S) R10, C(S)NR10R11, SR10, S(O)R10, SO$_2$R10, NHSO$_2$R10, SO$_2$NR10R11, —O—SO$_2$R10, —SO$_2$—O— R10, aryl, heteroaryl, formyl, trifluoromethyl, trifluoromethoxy or (1–6C)alkyl;

R1, R2, R8, R9, R10 and R11 are, independently of one another, a hydrogen, (1–6C)alkyl, aryl, alkenyl, alkynyl, heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, trifluoromethyl, trifluoromethoxy;

R1 and R2 or R8 and R9 or R10 and R11 can form a 5- or 6-membered ring which may or may not have a heteroatom, such as O, S or N;

and, when R3 is a 6-membered nitrogenous heteroaryl or a thiazolyl or an imidazolyl or an oxazolyl, then at least one of the R5 and R6 groups is an aryl which is optionally substituted by 1 or more substituents chosen from halogen, CN, NO$_2$, NH$_2$, OH, OR10, COOH, C(O)OR10, —O—C (O)R10, NR10R11, NHC(O)R10, C(O)NR10R11, NHC(S) R10, C(S)NR10R11, SR10, S(O)R10, SO$_2$R10, NHSO$_2$R10, SO$_2$NR10R11, —O—SO$_2$R10, —SO$_2$—O— R10, aryl, heteroaryl, formyl, trifluoromethyl, trifluoromethoxy or (1–6C)alkyl;

to their racemates, enantiomers or diastereoisomers and their mixtures, to their tautomers and to their pharmaceutically acceptable salts.

More particularly, the present invention relates to derivatives of formula (I) in which:

R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, $SO_2R1$, C(=NH)R1 or C(=NH)NR1 radical; these radicals optionally being substituted by 1 or more substituents chosen from halogen, CN, $NO_2$, $NH_2$, OH, OR1, COOH, C(O)OR1, —O—C(O)R1, NR1R2, NHC(O)R1, C(O)NR1R2, SR1, S(O)R1, $SO_2R1$, $NHSO_2R1$, $SO_2NR1R2$, C(S)NR1R2, NHC(S)R1, —O—$SO_2R1$, —$SO_2$—O—R1, aryl, heteroaryl, heterocycle, formyl, trifluoromethyl, trifluoromethylsulfanyl, trifluoromethoxy or (1–6C)alkyl;

R5 and R6 are chosen, independently of one another, from the following radicals: halogen, CN, NO2, $NH_2$, OH, COOH, C(O)OR8, —O—C(O)R8, NR8R9, NHC(O)R8, C(O)NR8R9, NHC(S)R8, C(S)NR8R9, SR8, S(O)R8, $SO_2R8$, $NHSO_2R8$, $SO_2NR8R9$, —O—$SO_2R8$, —$SO_2$—O—R8, trifluoromethyl, trifluoromethoxy, (1–6C)alkyl, (1–6C)alkoxy, aryl, aryl(1–6C)alkyl, heteroaryl, heteroaryl (1–6C)alkyl, heterocycle, cycloalkyl, alkenyl, alkynyl, adamantyl, polycycloalkyls; these radicals optionally being substituted by 1 or more substituents chosen from halogen, CN, $NO_2$, $NH_2$, OH, OR10, COOH, C(O)OR10, —O—C(O)R10, NR10R11, NHC(O)R10, C(O)NR10R11, NHC(S)R10, C(S)NR10R11, SR10, S(O)R10, $SO_2R10$, $NHSO_2R10$, $SO_2NR10R11$, —O—$SO_2R10$, —$SO_2$—O—R10, aryl, heteroaryl, formyl, trifluoromethyl, trifluoromethoxy or (1–6C)alkyl;

R7 is a halogen, methyl, cyclopropyl, CN, OH, methoxy, trifluoromethyl, ethylenyl, acetylenyl, trifluoromethoxy, $NO_2$, $NH_2$ or NMe2

R1, R2, R8, R9, R10 and R11 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, $NO_2$, $NH_2$, OH, COOH, COOalkyl, $CONH_2$, formyl, trifluoromethyl or trifluoromethoxy;

R1 and R2 or R8 and R9 or R10 and R11 can form a 5- or 6-membered ring which may or may not have a heteroatom, such as O, S or N;

and when R3 is a 6-membered nitrogenous heteroaryl or a thiazolyl, an imidazolyl or an oxazolyl, then at least one of the radicals R5 and R6 is an aryl optionally substituted by 1 or more substituents chosen from halogen, CN, $NO_2$, $NH_2$, OH, OR10, COOH, C(O)OR10, —O—C(O)R10, NR10R11, NHC(O)R10, C(O)NR10R11, NHC(S)R10, C(S) NR10R11, SR10, S(O)R10, $SO_2R10$, $NHSO_2R10$, $SO_2NR10R11$, —O—$SO_2R10$, —$SO_2$—O—R10, aryl, heteroaryl, formyl, trifluoromethyl, trifluoromethoxy, and (1–6C)alkyl;

to their racemates, enantiomers or diastereoisomers and their mixtures, to their tautomers and to their pharmaceutically acceptable salts.

The present invention preferably relates to derivatives of formula (I) in which:

R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, $SO_2R1$ or C(=NH)NR1 radical; these radicals optionally being substituted by 1 or more substituents chosen from halogen, CN, $NO_2$, $NH_2$, OH, OR1, COOH, C(O)OR1, —O—C(O)R1, NR1R2, NHC(O)R1, C(O)NR1R2, SR1, S(O)R1, $SO_2R1$, $NHSO_2R1$, $SO_2NR1R2$, C(S)NR1R2, NHC(S)R1, —O—$SO_2R1$, —$SO_2$—O—R1, aryl, heteroaryl, formyl, oxo, trifluoromethyl, trifluoromethylsulfanyl, trifluoromethoxy or (1–6C)alkyl;

R5 is an aryl;

R6 and R7 are, independently of one another, a halogen, methyl, cyclopropyl, CN, OH, methoxy, trifluoromethyl, ethylenyl, acetylenyl, trifluoromethoxy, $NO_2$, $NH_2$ or $NMe_2$ R1 and R2 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, $NO_2$, $NH_2$, OH, COOH, COOalkyl, $CONH_2$, formyl, oxo, trifluoromethyl or trifluoromethoxy;

R1 and R2 can form a 5- or 6-membered ring which may or may not have a heteroatom, such as O, S or N;

to their racemates, enantiomers, diastereoisomers and their mixtures, to their tautomers and to their pharmaceutically acceptable salts.

The present invention preferably relates to derivatives of formula (I) in which:

R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, $SO_2R1$ or C(=NH)NR1 radical; these radicals optionally being substituted by 1 or more substituents chosen from halogen, CN, $NO_2$, $NH_2$, OH, OR1, COOH, C(O)OR1, —O—C(O)R1, NR1R2, NHC(O)R1, C(O)NR1R2, SR1, S(O)R1, $SO_2R1$, $NHSO_2R1$, $SO_2NR1R2$, C(S)NR1R2, NHC(S)R1, —O—$SO_2R1$, —$SO_2$—O—R1, aryl, heteroaryl, formyl, oxo, trifluoromethyl, trifluoromethylsulfanyl, trifluoromethoxy or (1–6C)alkyl;

R5 is an aryl;

R6 is a halogen, methyl, cyclopropyl, CN, OH, methoxy, trifluoromethyl, ethylenyl, acetylenyl, trifluoromethoxy, $NO_2$, $NH_2$ or $NMe_2$;

R7 is a halogen

R1 and R2 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, $NO_2$, $NH_2$, OH, COOH, COOalkyl, $CONH_2$, formyl, oxo, trifluoromethyl or trifluoromethoxy;

R1 and R2 may form a 5- or 6-membered ring optionally containing a heteroatom such as O, S or N;

to their racemates, enantiomers or diastereoisomers and their mixtures, to their tautomers, and to their pharmaceutically acceptable salts.

In the preceding definitions and those which follow, the (1–6C) alkyl radicals comprise 1 to 6 carbon atoms in a straight- or branched-chain; the alkenyl radicals comprise 2 to 6 carbon atoms and one to 3 conjugated or nonconjugated double bonds in a straight- or branched-chain; the alkynyl radicals comprise 2 to 6 carbon atoms and one to 3 conjugated or nonconjugated triple bonds in a straight- or branched-chain; the aryl radicals are chosen from phenyl, naphthyl or indenyl; the heteroaryl radicals comprise 3 to 10 ring members, optionally comprising one or more heteroatoms chosen from oxygen, sulfur and nitrogen, in particular, thiazolyl, thienyl, pyrrolyl, pyridinyl, furyl, imidazolyl, oxazolyl, pyrazinyl, tetrazolyl, oxadiazolyl, thiadiazolyl, isoxadiazolyl, isothiadiazolyl, isothiazolyl, isoxazolyl, triazolyl, pyrazolyl or indolyl; the halogen radical is either chlorine, iodine, fluorine or bromine; the polycycloalkyl radicals are chosen from adamantyl, quinuclidinyl, bornanyl, norbornanyl, bornenyl or norbornenyl; the heteroaryl radicals fused to a (1–10C) cycloalkyl are chosen from indanyl, isochromanyl, chromanyl, 1,2,3,4-tetrahydroisoquinolyl or 1,2,3,4-tetrahydroquinolyl; the heterocycle radicals comprise 1 to 2 heteroatoms chosen from oxygen, sulfur or nitrogen and represent in particular piperidinyl, morpholinyl, pyrrolidinyl, imidazolidinyl, pyrazolidinyl, isothiazolidinyl, thiazolidinyl, isoxazolidinyl, oxazolidinyl, piperazinyl, azetidinyl, 2-piperidone, 3-piperidone, 4-piperidone, 2-pyrrolidone or 3-pyrrolidone.

The compounds of formula (I) exhibiting one or more asymmetric carbons and can therefore exist in the form of isomers, of racemates, of enantiomers and of diastereoisomers; the latter also form part of the invention, as do their mixtures.

Mention may be made, among the compounds of formula (I) of use according to the invention, of the following compounds:

N-(bicyclo[2.2.1]hept-5-en-2-ylmethyl)-6-chloro-7-fluoro-5-phenyl-1H-indazol-3-amine 6-chloro-7-fluoro-N-(3,3-dimethylbutyl)-5-phenyl-1H-indazol-3-amine 6-chloro-7-fluoro-N-(3-phenylpropyl)-5-phenyl-1H-indazol-3-amine 6-chloro-7-fluoro-N-(cyclopropylmethyl)-5-phenyl-1H-indazol-3-amine 6-chloro-7-fluoro-N-(cyclopentylmethyl)-5-phenyl-1H-indazol-3-amine 6-chloro-7-fluoro-N-[3-(methylthio)propyl]-5-phenyl-1H-indazol-3-amine 6-chloro-7-fluoro-N-(phenylethyl)-5-phenyl-1H-indazol-3-amine 6-chloro-7-fluoro-N-(cyclohexylmethyl)-5-phenyl-1H-indazol-3-amine 6-chloro-7-fluoro-N-propyl-5-phenyl-1H-indazol-3-amine 6-chloro-7-fluoro-N-(2,2,3,3,4,4,4-heptafluorobutyl)-5-phenyl-1H-indazol-3-amine hydrate 6-chloro-7-fluoro-N-(4,4,4-trifluorobutyl)-5-phenyl-1H-indazol-3-amine 6-chloro-7-fluoro-N-[(4-methoxyphenyl)methyl]-5-phenyl-1H-indazol-3-amine 6-chloro-7-fluoro-N-(phenylmethyl)-5-phenyl-1H-indazol-3-amine 6-chloro-7-fluoro-N- [(4-cyanophenyl)methyl]-5-phenyl-1H-indazol-3-amine N-[(4-chlorophenyl)methyl]-6-chloro-7-fluoro-5-phenyl-1H-indazol-3-amine 6-chloro-7-fluoro-N-[(3-methoxyphenyl)methyl]-5-phenyl-1H-indazol-3-amine 6-chloro-7-fluoro-N-[[4-(trifluoromethoxy)phenyl]methyl]-5-phenyl-1H-indazol-3-amine N-[4-[[[6-chloro-7-fluoro-5-phenyl-1H-indazol-3-yl]amino]methyl]phenyl]acetamide 6-chloro-7-fluoro-N-[(3,5-dichlorophenyl)methyl]-5-phenyl-1H-indazol-3-amine 6-chloro-7-fluoro-5-phenyl-N-[[4-(trifluoromethyl)phenyl]methyl]-1H-indazol-3-amine 6-chloro-7-fluoro-N-[(4-fluorophenyl)methyl]-5-phenyl-1H-indazol-3-amine 6-chloro-7-fluoro-N-[3-(4-methylphenoxy)phenylmethyl]-5-phenyl-1H-indazol-3-amine N-(2,2,3,3,4,4,4-heptafluorobutyl)-6-chloro-7-fluoro-5-phenyl-1H-indazol-3-amine 6-chloro-7-fluoro-5-phenyl-N-[[3,5-bis(trifluoromethyl)phenyl]methyl]-1H-indazol-3-amine 6-chloro-7-fluoro-5-phenyl-N-[[3-(trifluoromethyl)phenyl]methyl]-1H-indazol-3-amine 6-chloro-7-fluoro-N-[(6-methoxy-2-naphthyl)methyl]-5-phenyl-1H-indazol-3-amine 6-chloro-7-fluoro-N-[(pentafluorophenyl)methyl]-5-phenyl-1H-indazol-3-amine 6-chloro-7-fluoro-N-[[4-(methylthio)phenyl]methyl]-5-phenyl-1H-indazol-3-amine N-[(4-chloro-3-fluorophenyl)methyl]-6-chloro-7-fluoro-5-phenyl-1H-indazol-3-amine 6-chloro-7-fluoro-5-phenyl-N-(3,3,3-trifluoropropyl)-1H-indazol-3-amine 6-chloro-7-fluoro-5-phenyl-N-(3-thienylmethyl)-1H-indazol-3-amine N-(bicyclo[2.2.1]hept-5-en-2-ylmethyl)-6-chloro-7-fluoro-5-phenyl-1H-indazol-3-amine N-(1,1'-biphenyl-4-ylmethyl)-6-chloro-7-fluoro-5-phenyl-1H-indazol-3-amine 6-chloro-7-fluoro-N-[[4-(dimethylamino)phenyl]methyl]-5-phenyl-1H-indazol-3-amine N-(2,2'-bithiophen-5-ylmethyl)-6-chloro-7-fluoro-5-phenyl-1H-indazol-3-amine 6-chloro-7-fluoro-5-phenyl-N-[[1-(phenylmethyl)-1H-imidazol-2-yl]methyl]-1H-indazol-3-amine 6-chloro-7-fluoro-N-[[ 1-methyl-1H-imidazol-2-yl]methyl]-5-phenyl-1H-indazol-3-amine 6-chloro-7-fluoro-N-[(1-methyl-1H-indol-3-yl)methyl]-5-phenyl-1H-indazol-3-amine 6-chloro-7-fluoro-N-[(5-methyl-2-furanyl)methyl]-5-phenyl-1H-indazol-3-amine 6-chloro-7-fluoro-5-phenyl-N-(1H-pyrrol-2-ylmethyl)-1H-indazol-3-amine 6-chloro-7-fluoro-5-phenyl-N-[(1H-imidazol-2-yl)methyl]-1H-indazol-3-amine 6-chloro-7-fluoro-5-phenyl-N-[(1H-imidazol-4-yl)methyl]-1H-indazol-3-amine 6-chloro-7-fluoro-5-phenyl-N-(1H-pyrazol-3-ylmethyl)-1H-indazol-3-amine 6-chloro-7-fluoro-N-[[2-methyl-1H-imidazol-4-yl]methyl]-5-phenyl-1H-indazol-3-amine 6-chloro-7-fluoro-N-[(3,5-dimethyl-1-phenyl-1H-pyrazol-4-yl)methyl]-5-phenyl-1H-indazol-3-amine 6-chloro-7-fluoro-5-phenyl-N-[[2-phenyl-1H-imidazol-4-yl]methyl]-1H-indazol-3-amine 6-chloro-7-fluoro-N-[[5-(4-chlorophenyl)-2-furanyl]methyl]-5-phenyl-1H-indazol-3-amine 6-chloro-7-fluoro-5-phenyl-N-[(1-methyl-1H-pyrrol-2-yl)methyl]-1H-indazol-3-amine 4-[5-[[[6-chloro-7-fluoro-5-phenyl-1H-indazol-3-yl]amino]methyl]-2-furanyl]-benzenesulfonamide 6-chloro-7-fluoro-5-phenyl-N-(3-thienylmethyl)-1H-indazol-3-amine 6-chloro-7-fluoro-5-phenyl-N-[[2-phenyl-1H-imidazol-4-yl]methyl]-1H-indazol-3-amine ethyl 2-[[[6-chloro-7-fluoro-5-phenyl-1H-indazol-3-yl]amino]methyl]-5-(methylthio)-1H-imidazole-4-carboxylate 6-chloro-7-fluoro-5-phenyl-N-[[5-[4-(trifluoromethyl)phenyl-2-furanyl]methyl]-1H-indazol-3-amine 6-chloro-7-fluoro-5-phenyl-N-[2-(1-piperidinyl)ethyl]-1H-indazol-3-amine 6-chloro-7-fluoro-N-[2-(4-morpholinyl)ethyl]-5-phenyl-1H-indazol-3-amine N-(6-chloro-7-fluoro-5-phenyl-1H-indazol-3-yl)-N'-(3,5-dichlorophenyl)urea N-(6-chloro-7-fluoro-5-phenyl-1H-indazol-3-yl)-N'-(2-propenyl)urea N-(6-chloro-7-fluoro-5-phenyl-1H-indazol-3-yl)-N'-(phenylmethyl)urea
N-(6-chloro-7-fluoro-5-phenyl-1H-indazol-3-yl)-N'-(4-phenoxyphenyl)urea
N-(6-chloro-7-fluoro-5-phenyl-1H-indazol-3-yl)-N'-(4-methoxyphenyl)methyl]urea
N-(6-chloro-7-fluoro-5-phenyl-1H-indazol-3-yl)-N'-[4-(trifluoromethyl)phenyl]urea
N-(6-chloro-7-fluoro-5-phenyl-1H-indazol-3-yl)-N'-(4-methoxyphenyl)urea
N-(6-chloro-7-fluoro-5-phenyl-1H-indazol-3-yl)-N'-cyclohexylurea
N-(6-chloro-7-fluoro-5-phenyl-1H-indazol-3-yl)-N'-propylurea
N-(6-chloro-7-fluoro-5-phenyl-1H-indazol-3-yl)-N'-(4-chlorophenyl)urea
N-(6-chloro-7-fluoro-5-phenyl-1H-indazol-3-yl)-N'-(4-fluorophenyl)urea
N-[6-chloro-7-fluoro-5-phenyl-1H-indazol-3-yl]-N'-(tricyclo[3.3.1.1$^{3,7}$]dec)-1-ylurea
N-(6-chloro-7-fluoro-5-phenyl-1H-indazol-3-yl)-N'-(4-methylphenyl)urea
N-(6-chloro-7-fluoro-5-phenyl-1H-indazol-3-yl)urea
N-(6-chloro-7-methyl-5-phenyl-1H-indazol-3-yl)urea
N-(6-chloro-7-cyano-5-phenyl-1H-indazol-3-yl)urea
N-(6-chloro-7-cyclopropyl-5-phenyl-1H-indazol-3-yl)urea
N-(6-chloro-7-hydroxy-5-phenyl-1H-indazol-3-yl)urea
N-(6-chloro-7-methoxy-5-phenyl-1H-indazol-3-yl)urea
N-(6-chloro-7-trifluoromethyl-5-phenyl-1H-indazol-3-yl)urea
N-(6-chloro-7-trifluoromethoxy-5-phenyl-1H-indazol-3-yl)urea
N-(6-chloro-7-nitro-5-phenyl-1H-indazol-3-yl)urea
N-(6-chloro-7-amino-5-phenyl-1H-indazol-3-yl)urea
N-(6-chloro-7-dimethylamino-5-phenyl-1H-indazol-3-yl)urea
N-(6-chloro-7-ethynyl-5-phenyl-1H-indazol-3-yl)urea
N-[6-chloro-7-fluoro-5-phenyl-1H-indazol-3-yl]-4-methyl-benzenesulfonamide
N-[6-chloro-7-fluoro-5-phenyl-1H-indazol-3-yl]methanesulfonamide
N-[6-chloro-7-fluoro-5-phenyl-1H-indazol-3-yl]-2-propanesulfonamide
N-[6-chloro-7-fluoro-5-phenyl-1H-indazol-3-yl]-2,2,2-trifluoroethanesulfonamide
N-[6-chloro-7-fluoro-5-phenyl-1H-indazol-3-yl]-2-thiophenesulfonamide
N-[6-chloro-7-fluoro-5-phenyl-1H-indazol-3-yl]benzenesulfonamide
N-[6-chloro-7-fluoro-5-phenyl-1H-indazol-3-yl]-4-(trifluoromethyl)benzenesulfonamide
N-[6-chloro-7-fluoro-5-phenyl-1H-indazol-3-yl]-5-(3-isoxazolyl)-2-thiophenesulfonamide
N-[6-chloro-7-fluoro-5-phenyl-1H-indazol-3-yl]-4-fluorobenzenesulfonamide
N-[6-chloro-7-fluoro-5-phenyl-1H-indazol-3-yl]-4-methoxybenzenesulfonamide
N-[6-chloro-7-fluoro-5-phenyl-1H-indazol-3-yl]benzenemethanesulfonamide
N-[6-chloro-7-fluoro-5-phenyl-1H-indazol-3-yl]-1-methyl-1H-imidazole-4-sulfonamide
N-[6-chloro-7-fluoro-5-phenyl-1H-indazol-3-yl]-4-(1,1-dimethylethyl)benzenesulfonamide
N-[4-[[(6-chloro-7-fluoro-5-phenyl-1H-indazol-3-yl)amino]sulfonyl]phenyl]-acetamide
N-[6-chloro-7-fluoro-5-phenyl-1H-indazol-3-yl]-4-methylbenzenemethanesulfonamide
6-chloro-7-fluoro-N-(pentafluorophenyl)-5-phenyl-1H-indazol-3-amine
6-chloro-7-fluoro-N-(3,4-difluorophenyl)-5-phenyl-1H-indazol-3-amine
6-chloro-7-fluoro-5-phenyl-N-(2,3,5,6-tetrafluorophenyl)-1H-indazol-3-amine
6-chloro-7-fluoro-5-phenyl-N-(2,4,6-trifluorophenyl)-1H-indazol-3-amine
6-chloro-7-fluoro-N-(4-fluorophenyl)-5-phenyl-1H-indazol-3-amine
6-chloro-7-fluoro-N-[3-(trifluoromethyl)phenyl]-5-phenyl-1H-indazol-3-amine
6-chloro-7-fluoro-N-[4-(trifluoromethyl)phenyl]-5-phenyl-1H-indazol-3-amine
6-chloro-7-fluoro-N-[3-fluoro-5-(trifluoromethyl)phenyl]-5-phenyl-1H-indazol-3-amine
6-chloro-7-fluoro-N-(4-nitrophenyl)-5-phenyl-1H-indazol-3-amine
6-chloro-7-fluoro-N-(3-nitrophenyl)-5-phenyl-1H-indazol-3-amine
6-chloro-7-fluoro-N-(3-methoxyphenyl)-5-phenyl-1H-indazol-3-amine
6-chloro-7-fluoro-N-(4-methoxyphenyl)-5-phenyl-1H-indazol-3-amine
6-chloro-7-fluoro-N,5-diphenyl-1H-indazol-3-amine
6-chloro-7-fluoro-N-(1-pyridinyl)-5-phenyl-1H-indazol-3-amine
6-chloro-7-fluoro-N-(2-pyridinyl)-5-phenyl-1H-indazol-3-amine
N-butyl-6-chloro-7-fluoro-5-phenyl-1H-indazol-3-amine
N-(6-chloro-7-fluoro-5-phenyl-1H-indazol-3-yl)-N'-phenylurea
N-(6-chloro-7-fluoro-5-phenyl-1H-indazol-3-yl)-3-methoxybenzenesulfonamide
their isomers, their mixtures, their racemates, enantiomers, diastereoisomers or tautomers, and their pharmaceutically acceptable salts, and more particularly the following compound:
Piperidine-1-carboxylic acid (6,7-difluoro-5-phenyl-1H-indazol-3-yl)amide
Pyrrolidine-1-carboxylic acid (6,7-difluoro-5-phenyl-1H-indazol-3-yl)amide
1-(6,7-Difluoro-5-phenyl-1H-indazol-3-yl)-3-[3-(4-methylpiperazin-1-yl)propyl]urea
N-(6,7-Difluoro-5-phenyl-1H-indazol-3-yl)-N'-phenylurea
its tautomers, and their pharmaceutically acceptable salts,
The invention also relates to the pharmaceutical compositions comprising, as active principle, a derivative of formula (I) in which
R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1, C(=NH)R1 or C(=NH)NR1 radical; these radicals optionally being substituted by 1 or more substituents chosen from CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, heterocycle, formyl, trifluoromethyl, trifluoromethylsulfanyl, trifluoromethoxy or (1–6C)alkyl;
R5, R6 and R7 are, independently of one another, chosen from the following radicals halogen, CN, NO2, NH$_2$, OH, COOH, C(O)OR8, —O—C(O)R8, NR8R9, NHC(O)R8, C(O)NR8R9, NHC(S)R8, C(S)NR8R9, SR8, S(O)R8, SO$_2$R8, NHSO$_2$R8, SO$_2$NR8R9, —O—SO$_2$R8, -SO$_2$—O—R8, trifluoromethyl, trifluoromethoxy, (1–6C)alkyl, (1–6C) alkoxy, aryl, aryl(1–6C)alkyl, heteroaryl, heteroaryl(1–6C) alkyl, heterocycle, cycloalkyl, alkenyl, alkynyl, adamantyl or polycycloalkyl; these radicals optionally being substituted by 1 or more substituents chosen from halogen, CN, NO$_2$, NH$_2$, OH, OR10, COOH, C(O)OR10, —O—C(O) R10, NR10R11, NHC(O)R10, C(O)NR10R11, NHC(S)R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C) alkyl;

R1, R2, R8, R9, R10 and R11 are, independently of one another, a hydrogen, (1–6C)alkyl, aryl, alkenyl, alkynyl, heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, trifluoromethyl, trifluoromethoxy;

R1 and R2 or R8 and R9 or R10 and R11 can form a 5- or 6-membered ring which may or may not have a heteroatom, such as O, S or N;

and, when R3 is a 6-membered nitrogenous heteroaryl or a thiazolyl or an imidazolyl or an oxazolyl, then at least one of the R5 and R6 groups is an aryl which is optionally substituted by 1 or more substituents chosen from halogen, CN, NO$_2$, NH$_2$, OH, OR10, COOH, C(O)OR10, —O—C (O)R10, NR10R11, NHC(O)R10, C(O)NR10R11, NHC(S) R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;

to their racemates, enantiomers or diastereoisomers and their mixtures, to their tautomers and to their pharmaceutically acceptable salts.

The present invention relates more particularly to the pharmaceutical compositions comprising, as active principle, a derivative of formula (I) in which:

R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1, C(=NH)R1 or C(=NH)NR1 radical; these radicals optionally being substituted by 1 or more substituents chosen from halogen, CN, NO$_2$, NH$_2$, OH, OR1, COOH, C(O)OR1, —O—C(O)R1, NR1R2, NHC (O)R1, C(O)NR1R2, SR1, S(O)R1, SO$_2$R1, NHSO$_2$R1, SO$_2$NR1R2, C(S)NR1R2, NHC(S)R1, —O—SO$_2$R1, -SO$_2$—O—R1, aryl, heteroaryl, heterocycle, formyl, trifluoromethyl, trifluoromethylsulfanyl, trifluoromethoxy or (1–6C)alkyl;

R5 and R6 are chosen, independently of one another, from the following radicals: halogen, CN, NO2, NH$_2$, OH, COOH, C(O)OR8, —O—C(O)R8, NR8R9, NHC(O)R8, C(O)NR8R9, NHC(S)R8, C(S)NR8R9, SR8, S(O)R8, SO$_2$R8, NHSO$_2$R8, SO$_2$NR8R9, —O—SO$_2$R8, —SO$_2$—O—R8, trifluoromethyl, trifluoromethoxy, (1–6C)alkyl, (1–6C)alkoxy, aryl, aryl(1–6C)alkyl, heteroaryl, heteroaryl (1–6C)alkyl, heterocycle, cycloalkyl, alkenyl, alkynyl, adamantyl, polycycloalkyls; these radicals optionally being substituted by 1 or more substituents chosen from halogen, CN, NO$_2$, NH$_2$, OH, OR10, COOH, C(O)OR10, —O—C (O)R10, NR10R11, NHC(O)R10, C(O)NR10R11, NHC(S) R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;

R7 is a halogen, methyl, cyclopropyl, CN, OH, methoxy, trifluoromethyl, ethylenyl, acetylenyl, trifluoromethoxy, NO$_2$, NH$_2$ or NMe2

R1, R2, R8, R9, R10 and R11 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, trifluoromethyl or trifluoromethoxy;

R1 and R2 or R8 and R9 or R10 and R11 can form a 5- or 6-membered ring which may or may not have a heteroatom, such as O, S or N;

and when R3 is a 6-membered nitrogenous heteroaryl or a thiazolyl, imidazolyl or oxazolyl, then at least one of the radicals R5 and R6 is an aryl optionally substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)R10, C(S) NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy and (1–6C)alkyl;

to their racemates, enantiomers or diastereoisomers and their mixtures, to their tautomers and to their pharmaceutically acceptable salts.

The present invention preferably relates to the pharmaceutical compositions comprising, as active principle, a derivative of formula (I) in which:

R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1 or C(=NH)NR1 radical; these radicals optionally being substituted by 1 or more substituents chosen from halogen, CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, formyl, oxo, trifluoromethyl, trifluoromethylsulfanyl, trifluoromethoxy or (1–6C) alkyl;

R5 is an aryl;

R6 and R7 are, independently of one another, a halogen, methyl, cyclopropyl, CN, OH, methoxy, trifluoromethyl, ethylenyl, acetylenyl, trifluoromethoxy, NO$_2$, NH$_2$, NMe$_2$ R1 and R2 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, trifluoromethyl or trifluoromethoxy;

R1 and R2 may form a 5- or 6-membered ring optionally containing a heteroatom such as O, S or N;

to their racemates, enantiomers or diastereoisomers and to their mixtures, their tautomers, and to their pharmaceutically acceptable salts.

The present invention also relates to the use, as medicament, of the aminoindazole derivatives of the formula (I) in which:

R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1, C(=NH)R1 or C(=NH)NR1 radical; these radicals optionally being substituted by 1 or more substituents chosen from CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, heterocycle, formyl, trifluoromethyl, trifluoromethylsulfanyl, trifluoromethoxy or (1–6C)alkyl;

R5, R6 and R7 are, independently of one another, chosen from the following radicals halogen, CN, NO2, NH$_2$, OH, COOH, C(O)OR8, —O—C(O)R8, NR8R9, NHC(O)R8, C(O)NR8R9, NHC(S)R8, C(S)NR8R9, SR8, S(O)R8, SO$_2$R8, NHSO$_2$R8, SO$_2$NR8R9, —O—SO$_2$R8, —SO$_2$—O—R8, trifluoromethyl, trifluoromethoxy, (1–6C)alkyl, (1–6C)alkoxy, aryl, aryl(1–6C)alkyl, heteroaryl, heteroaryl (1–6C)alkyl, heterocycle, cycloalkyl, alkenyl, alkynyl, adamantyl or polycycloalkyl; these radicals optionally being substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S) R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;

R1, R2, R8, R9, R10 and R11 are, independently of one another, a hydrogen, (1–6C)alkyl, aryl, alkenyl, alkynyl, heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, trifluoromethyl, trifluoromethoxy;

R1 and R2 or R8 and R9 or R10 and R11 can form a 5- or 6-membered ring which may or may not have a heteroatom, such as O, S or N;

and, when R3 is a 6-membered nitrogenous heteroaryl or a thiazolyl or an imidazolyl or an oxazolyl, then at least one of the R5 and R6 groups is an aryl which is optionally substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S) R10, C(S)NR10R11, SR10, S(O)R10, SO$_2$R10, NHSO$_2$R10, SO$_2$NR1OR11, —O—SO$_2$R10, —SO$_2$—O—R10, aryl, heteroaryl, formyl, trifluoromethyl, trifluoromethoxy or (1–6C)alkyl;

to their racemates, enantiomers or diastereoisomers and their mixtures, to their tautomers and to their pharmaceutically acceptable salts.

The present invention relates more particularly to the use, as medicament, of the aminoindazole derivatives of formula (I) in which:

R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1, C(=NH)R1 or C(=NH)NR1 radical; these radicals optionally being substituted by 1 or more substituents chosen from halogen, CN, NO$_2$, NH$_2$, OH, OR1, COOH, C(O)OR1, —O—C(O)R1, NR1R2, NHC (O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, heterocycle, formyl, trifluoromethyl, trifluoromethylsulfanyl, trifluoromethoxy or (1–6C)alkyl;

R5 and R6 are chosen, independently of one another, from the following radicals: halogen, CN, NO2, NH$_2$, OH, COOH, C(O)OR8, —O—C(O)R8, NR8R9, NHC(O)R8, C(O)NR8R9, NHC(S)R8, C(S)NR8R9, SR8, S(O)R8, SO$_2$R8, NHSO$_2$R8, SO$_2$NR8R9, —O—SO$_2$R8, —SO$_2$—O—R8, trifluoromethyl, trifluoromethoxy, (1–6C)alkyl, (1–6C)alkoxy, aryl, aryl(1–6C)alkyl, heteroaryl, heteroaryl (1–6C)alkyl, heterocycle, cycloalkyl, alkenyl, alkynyl, adamantyl, polycycloalkyls; these radicals optionally being substituted by 1 or more substituents chosen from halogen, CN, NO$_2$, NH$_2$, OH, OR10, COOH, C(O)OR10, —O—C (O)R10, NR10R11, NHC(O)R10, C(O)NR10R11, NHC(S) R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;

R7 is a halogen, methyl, cyclopropyl, CN, OH, methoxy, trifluoromethyl, ethylenyl, acetylenyl, trifluoromethoxy, NO$_2$, NH$_2$ or NMe2

R1, R2, R8, R9, R10 and R11 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, trifluoromethyl or trifluoromethoxy;

R1 and R2 or R8 and R9 or R10 and R11 can form a 5- or 6-membered ring which may or may not have a heteroatom, such as O, S or N;

and, when R3 is a 6-membered nitrogenous heteroaryl or a thiazolyl or an imidazolyl or an oxazolyl, then at least one of the R5 and R6 groups is an aryl which is optionally substituted by 1 or more substituents chosen from halogen, CN, NO$_2$, NH$_2$, OH, OR10, COOH, C(O)OR10, —O—C (O)R10, NR10R11, NHC(O)R10, C(O)NR10R11, NHC(S) R10, C(S)NR1, OR11, SR10, S(O)R10, SO$_2$R10, NHSO$_2$R10, SO$_2$NR1OR11, —O—SO$_2$R10, —SO$_2$—O—R10, aryl, heteroaryl, formyl, trifluoromethyl, trifluoromethoxy or (1–6C)alkyl;

to their racemates, enantiomers or diastereoisomers and their mixtures, to their tautomers and to their pharmaceutically acceptable salts.

The present invention preferably relates to the use, as medicament, of the aminoindazole derivatives of formula (I) in which:

R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1 or C(=NH)NR1 radical; these radicals optionally being substituted by 1 or more substituents chosen from halogen, CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, formyl, oxo, trifluoromethyl, trifluoromethylsulfanyl, trifluoromethoxy or (1–6C) alkyl;

R5 is an aryl;

R6 and R7 are, independently of one another, a halogen, methyl, cyclopropyl, CN, OH, methoxy, trifluoromethyl, ethylenyl, acetylenyl, trifluoromethoxy, NO$_2$, NH$_2$ or NMe$_2$ R1 and R2 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, oxo, trifluoromethyl or trifluoromethoxy;

R1 and R2 may form a 5- or 6-membered ring optionally containing a heteroatom such as O, S or N;

to their racemates, enantiomers or diastereoisomers and to their mixtures, their tautomers, and to their pharmaceutically acceptable salts.

The derivatives of formula (1) can be obtained from the corresponding 3-amino derivatives (V) for which the nitrogen in the 1-position is optionally protected with a group Pr. Pr is a trimethylsilylethoxymethyl, tosyl, mesyl or benzyl radical or the groups known for the protection of the NH groups of aromatic heterocycles as indicated in T. W. Greene, Protective Groups in Organic Synthesis, J. Wiley-Interscience Publication (1999)

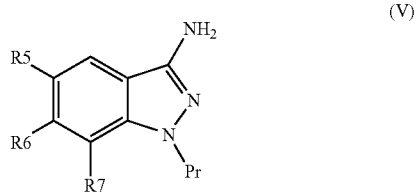

The 3-amino 1H-indazoles of formula (II) can be obtained by reaction of a 2-fluorobenzonitrile with hydrazine hydrate or hydrochloride at reflux for 2 to 18 hours in an alcohol of ethanol or n-butanol type according to R. F. Kaltenbach, Bioorg. Med. Chem. Lett., 9(15), 2259–62 (1999):

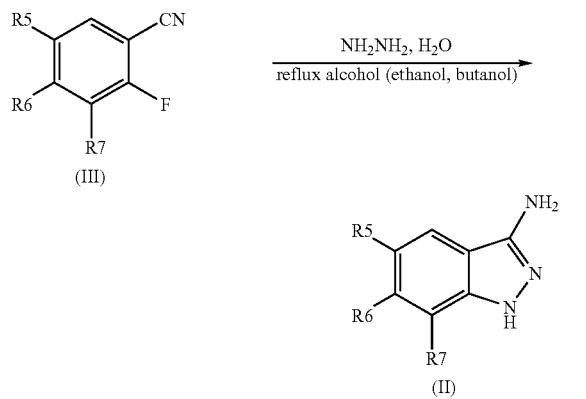

The compounds for which R5 and R6 are, independently of one another, chosen from the following radicals: halogen, CN, NO₂, NH₂, OH, COOH, C(O)OR8, —O—C(O)R8, NR8R9, NHC(O)R8, C(O)NR8R9, NHC(S)R8, C(S)NR8R9, SR8, S(O)R8, SO₂R8, NHSO₂R8, SO₂NR8R9, —O—SO₂R8, —SO₂—O—R8, trifluoromethyl, trifluoromethoxy, (1–6C)alkyl, (1–6C)alkoxy, aryl, aryl(1–6C)alkyl, heteroaryl, heteroaryl(1–6C)alkyl, cycloalkyl, alkenyl, alkynyl or adamantyl; these radicals optionally being substituted by 1 or more substituents chosen from halogen, CN, NO₂, NH₂, OH, OR10, COOH, C(O)OR10, —O—C(O)R10, NR10R11, NHC(O)R10, C(O)NR10R11, NHC(S)R10, C(S)NR10R11, SR10, S(O)R10, SO₂R10, NHSO₂R10, SO₂NR10R11, —O—SO₂R10, —SO₂—O—R10, aryl, heteroaryl, formyl, oxo, trifluoromethyl, trifluoromethoxy or (1–6C)alkyl; can be obtained by reactions involving the chemistry of palladium: Suzuki (A. Suzuki, Pure Appl. Chem., 63, 419–22 (1991), Stille (J. Stille, Angew. Chem., Int. Ed., 25, 508–24 (1986)), Heck (R. F. Heck, Org. React., 27, 345–90 (1982)), Sonogashira, (K. Sonogashira, Synthesis, 777 (1977)), Buckwald (S. L. Buckwald, Acc. Chem. Re., 31, 805 (1998)), from the corresponding halogenated derivatives.

For this, it is necessary to protect the reactive functional groups. Thus, the OH, SH, COOH and NH₂ functional groups must be protected before carrying out the coupling. The protective groups are introduced according to any method known to a person skilled in the art and in particular those described by T. W. Greene, Protective groups in Organic Synthesis, J. Wiley-Interscience Publication (1999). It is preferable to protect the nitrogen in the 1-position with groups such as tert-butoxycarbonyl or silicon derivatives. The choice will preferably be made of a tert-butyldimethylsilyl or triisopropylsilyl silyl group which can be removed by fluoride anions or with acetic acid and more particularly a trimethylsilylethoxymethyl group which can be cleaved by tetrabutylammonium fluoride at reflux in solvents such as tetrahydrofuran or dioxane (J. P. Whitten, J. Org. Chem., 51, 1891 (1986); B. H. Lipshutz, Tetrahedron Lett., 4095 (1986)) or by 2N hydrochloric acid in methanol or ethanol at reflux.

The derivatives protected in the 1-position with trimethylsilylethoxymethyl are obtained by reacting the starting compound with trimethylsilylethoxymethyl chloride in the presence of sodium hydride in a solvent, such as dimethylformamide, at ambient temperature (J. P. Whitten, J. Org. Chem., 51, 1891 (1986); M. P. Edwards, Tetrahedron, 42, 3723 (1986)).

Likewise, the 1-NH nitrogen functional group of the indazole will be protected by groups such as silyl derivatives, benzyl, carbamate or tosyl. For example, in the case where it would be desired to carry out coupling with palladium to a derivative halogenated in the 6-position, it will be necessary to protect the nitrogen in the 1-position as shown below (X=Cl, Br or I):

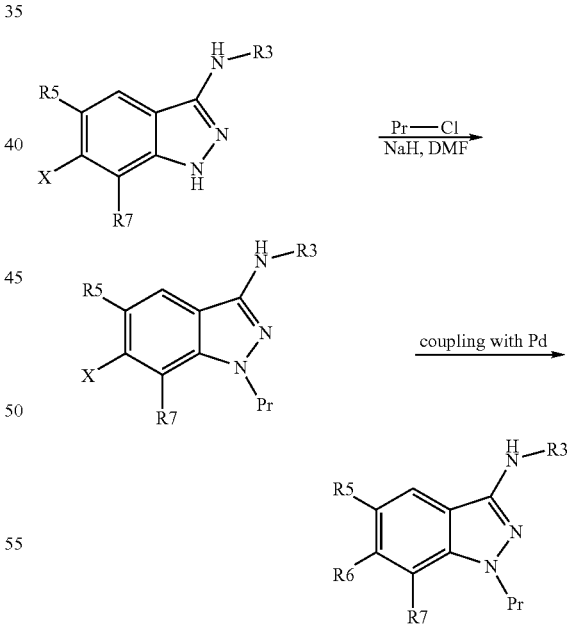

Deprotection is carried out according to methods known to a person skilled in the art and described by T. W. Greene, Protective Groups in Organic Synthesis, J. Wiley-Interscience Publication (1999). For example, if the protective group in the 1-position is a trimethylsilylethoxymethyl, it can be deprotected by reaction with tetrabutylammonium fluoride as shown below:

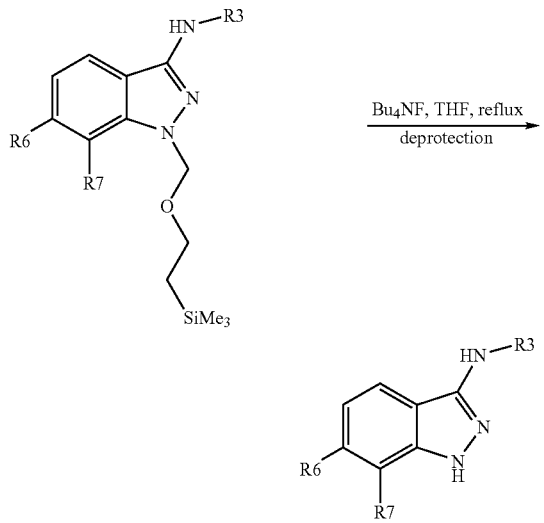

When one of the R5 or R6 groups involved in the coupling using the chemistry of palladium itself comprises a reactive functional group, such as hydroxyl, amine, thiol or acid or generally includes a heteroatom, it is also necessary to protect the latter before carrying out the coupling with palladium. Thus, for example, a phenol functional group will be introduced in the protected form (O-benzyl, for example) from the chlorinated derivative, the nitrogen in the 1-position being protected as explained previously:

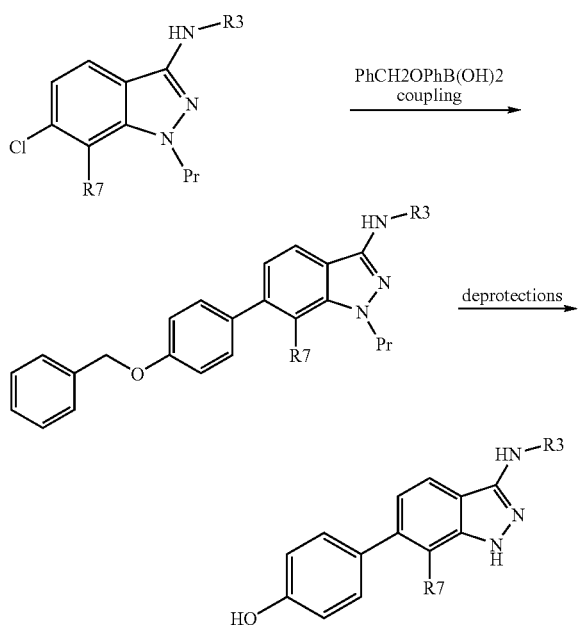

The benzyl group will subsequently be removed, for example by treatment with trimethylsilyl iodide at reflux in acetonitrile. Protection can also be carried out by a trimethylsilylethoxymethyl group which can be cleaved by tetrabutylammonium fluoride at reflux in solvents such as tetrahydrofuran or dioxane. (J. P. Whitten, J. Org. Chem., 51, 1891 (1986); B. H. Lipshutz, Tetrahedron Lett., 4095 (1986)) or by 2N hydrochloric acid in methanol or ethanol at reflux.

When R5 and R6 are, independently of one another, an aryl and a halogen, the aryl functional group is introduced from coupling with palladium to a brominated position, the nitrogen in the 1- and 3-positions being appropriately protected. Preferably, Pr represents a trimethylsilylethoxymethyl and Pr' represents an n-butylcarbonyl group which forms, with the nitrogen, an n-butylamide. The stage of deprotecting the amide is carried out in the presence of ethanolamine at reflux for one week in DMF. This cleavage can also be carried out with stannous chloride in ethanol (R. J. Griffin, J. Chem. Soc. Perkin I, 1992, 1811–1819) or else sodium methoxide in methanol (Y. Furukawa, Chem. Pharm. Bull., 1968, 16, 1076) or any other alkoxide in the corresponding alcohol.

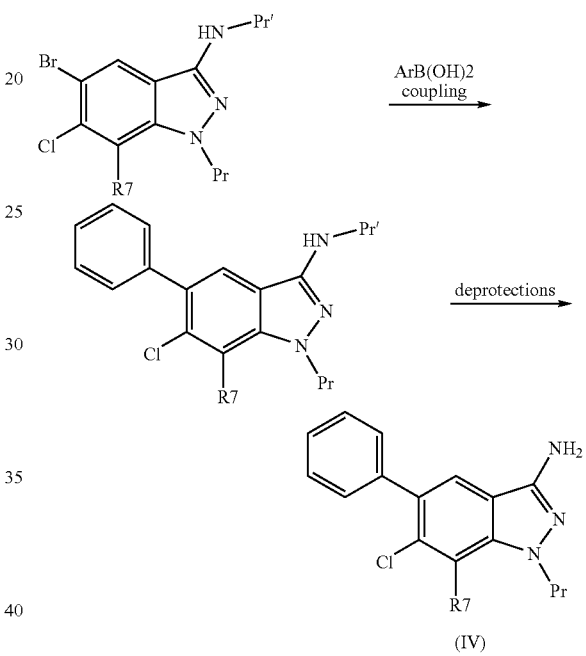

When R5 and R6 are, independently of one another, an aryl and a halogen, the aryl functional group is introduced from coupling with palladium to a brominated position, the nitrogen in the 1-and 3-positions being appropriately protected. Preferably, Pr represents a trimethylsilylethoxymethyl and Pr' represents an n-butylcarboxy group which forms, with the nitrogen, an n-butylamide. The electrophilic substitution is carried out, for example, with nitronium tetrafluoroborate ($NO_2BF_4$). The coupling of the 5-position is performed using palladium chemistry (Suzuki, Heck or Sonogashira coupling). The 7-position is functionalized, as a function of the desired substituents, by reductions, halogenations to introduce a bromine, or coupling by palladium chemistry (Suzuki, Heck or Sonogashira coupling) to introduce aryl, heteroaryl, alkyl, alkenyl, alkynyl or acetylenic functions. The stage of deprotecting the amide is carried out in the presence of ethanolamine at reflux for one week in DMF. This cleavage can also be carried out with stannous chloride in ethanol (R J Griffin, J. Chem. Soc. Perkin I, 1992, 1811–1819) or else sodium methoxide in methanol (Y. Furukawa, Chem. Pharm. Bull., 1968, 16, 1076) or any other alkoxide in the corresponding alcohol. The deprotection in the 3-position produces the $NH_2$ functional group, which can react with the necessary groups to introduce the desired substitutions into the 3-position as described in the following pages.

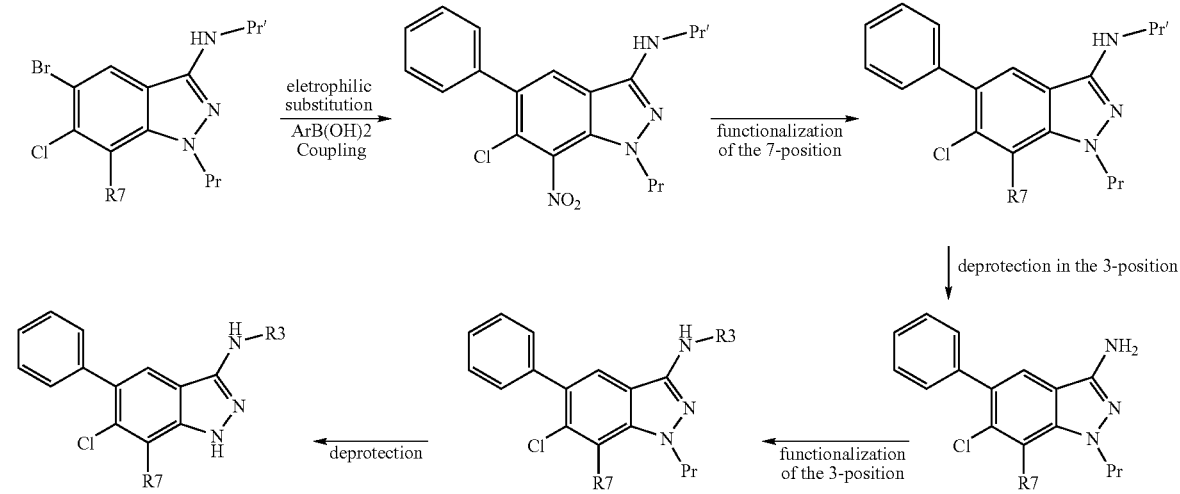

The compounds of formula (II) are the starting point for the preparation of a great variety of products obtained by reaction of the primary amine functional group of the 3-aminoindazole in all the conventional reactions of this functional group, such as: alkylation, acylation, reactions with carbonyl derivatives followed by reduction, sulfonation, conversion to ureas or carbamates, arylation (Castro reaction or Buchwald reaction), and the like.

The reductive aminations of derivatives of general formula (I) where R3 is H when Pr is trimethylsilylethoxymethyl can be carried out using boron derivatives, such as sodium triacetoxyborohydride, in dichloromethane in the presence of an aldehyde of type R1CHO under the conditions described in Organic Reactions, Vol. 59, 1–714 (E. Baxter, A. Reitz), or by the other reducing agents commonly used to reduce imines, to form products where R3 is (1–6C)alkyl, aryl(1–6C)alkyl, heteroaryl(1–6C)alkyl, heterocycloalkyl, cycloalkyl or polycycloalkyl, these radicals optionally being substituted by 1 or more substituents chosen from halogen, CN, $NO_2$, $NH_2$, OH, OR1, COOH, C(O)OR1, —O—C(O)R1, NR1R2, NHC(O)R1, C(O)NR1R2, SR1, S(O)R1, $SO_2$R1, $NHSO_2$R1, $SO_2$NR1R2, C(S)NR1R2, NHC(S)R1, —O—$SO_2$R1, —$SO_2$—O—R1, aryl, heteroaryl, formyl, oxo, trifluoromethyl, trifluoromethylsulfanyl, trifluoromethoxy or (1–6C)alkyl.

Condensations of derivatives of general formula (I) where R3 is H with isocyanates of type OCNR1 can be carried out in particular in tetrahydrofuran and according to the examples described in Comprehensive Organic Functional Group Transformations, Vol. 6 (Katritzky, Meth-Cohn, Rees 1995), to form products where R3 is CONR1R2 or CSNR1R2, R1 and R2 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, $NO_2$, $NH_2$, OH, COOH, COOalkyl, $CONH_2$, formyl, oxo, trifluoromethyl or trifluoromethoxy.

Sulfonations of derivatives of general formula (I) where R3 is H can be carried out from a sulfonyl chloride of $R1SO_2Cl$ type in the presence of a base (in particular tertiary amines, such as triethylamine, or aromatic amines, such as pyridine) in a conventional solvent, such as, for example, dichloromethane, to form the products where R3 is $SO_2$R1 and R1 is a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, $NO_2$, $NH_2$, OH, COOH, COOalkyl, $CONH_2$, formyl, oxo, trifluoromethyl or trifluoromethoxy.

The compounds of formula (I) are isolated and can be purified by the usual known methods, for example by crystallization, chromatography or extraction.

The compounds of formula (I) can optionally be converted to addition salts with an inorganic or organic acid by the action of such an acid in an organic solvent, such as an alcohol, ketone, an ether or a chlorinated solvent. These salts also form part of the invention.

Mention may be made, as examples of pharmaceutically acceptable salts, of the following salts: benzenesulfonate, hydrobromide, hydrochloride, citrate, ethanesulfonate, fumarate, gluconate, iodate, maleate, isethionate, methanesulfonate, methylenebis-β-oxynaphthoate, nitrate, oxalate, pamoate, phosphate, salicylate, succinate, sulfate, tartrate, theophyllineacetate and p-toluenesulfonate.

The compounds of formula (I) are kinase inhibitors and are thus of use in the prevention and treatment of neurodegenerative diseases, Alzheimer's disease, Parkinson's disease, frontoparietal dementia, corticobasal degeneration, Pick's disease, strokes, cranial and spinal traumas and peripheral neuropathies, obesity, essential hypertension, atherosclerotic cardiovascular diseases, polycystic ovaries syndrome, syndrome X, immunodeficiency and cancer.

The activities were determined by measuring the inhibition of the phosphorylation of the tau protein in adult rat cortex sections.

Cortex sections with a thickness of 300 μm are prepared from male OFA rats (Iffa-Credo) aged 8–10 weeks, sacrificed by decapitation. They are incubated in 5 ml of DMEM medium comprising pyruvate and glucose 4.5 g/l at 37° C. for 40 min. The sections are subsequently washed twice with the medium, distributed in microtubes (50 μl in 500 μl of medium, with or without test compounds) and incubated at 37° C. with stirring. Two hours later, the experiment is halted by centrifuging. The sections are lyzed, sonicated and centrifuged at 18300 g for 15 min at 4° C. The concentration of proteins in the supernatant is determined by a commercial assay (BCA Protein Assay, Pierce) based on the Lowry method.

The samples, denatured beforehand at 70° C. for 10 min, are separated on 4–12% Bis-tris vertical gel in the presence of MOPS-SDS buffer and are electrotransferred onto a nitrocellulose membrane. Immunolabeling is carried out with the monoclonal antibody AD2, which specifically recognizes the Ser396/404 phosphorylated epitopes of the tau protein. The immunoreactive proteins are visualized by addition of a second antibody directed against mouse IgGs and coupled to peroxidase and of a chemoluminescent substrate. The autoradiograms obtained are finally quantified using the 'GeneTools' software from Syngene (GeneGnome, Ozyme) to determine an $IC_{50}$ value.

The compounds of formula (I) exhibit a highly advantageous activity and in particular some compounds have an $IC_{50}$ value of less than 100 µM.

The following examples illustrate the invention without implied limitation.

The conditions for analysis of the products by LC/MS were produced on a Waters Alliance 2695 device for the LC part and a Waters-Micromass Platform II for the mass part.

Preparation of the intermediate products:

6,7-Difluoro-1H-inidazole-3-amine 0.32 cm³ of hydrazine monohydrate is added to 0.46 cm³ of 2,3,4-trifluorobenzonitrile in 10 cm³ of absolute ethanol. The medium is heated at about 75° C. for 17 hours, followed by addition of 10 cm³ of ethyl acetate, 5 cm³ of tetrahydrofuran and 5 cm³ of distilled water. The organic phase is separated out after settling the phases and is washed with 10 cm³ of distilled water and then with 10 cm³ of saturated aqueous sodium chloride solution. The organic phase is separated out after settling the phases, dried over magnesium sulfate, filtered and concentrated to dryness under reduced pressure (2 kPa; 50° C.). The residue obtained is purified by chromatography under an argon pressure of 50 kPa, on a column of silica gel (particle size 40–60 µm; diameter 1.5 cm), eluting with a cyclohexane/ethyl acetate mixture (50/50 by volume). The fractions containing the expected product are combined and then evaporated under reduced pressure (2 kPa; 40° C.); after drying (90 Pa; 40° C.), 100 mg of 6,7-difluoro-1H-indazole-3-amine are obtained in the form of a white solid melting at 183° C.

¹H NMR spectrum (300 MHz, $(CD_3)_2SO$ d6, δ in ppm): 5.57 (unresolved complex: 2H); 6.93 (mt: 1H); 7.52 (ddd, J=8.5–4.5 and 1 Hz: 1H); 12.01 (unresolved complex: 1H).

N-(6,7-Difluoro-1H-indazol-3-yl)butanamide 0.61 cm³ of butyryl chloride is added to 1 g of 6,7-difluoro-1H-indazole-3-amine described above, in 15 cm³ of pyridine, after having cooled to about 3° C., and the mixture is then left at ambient temperature for 76 hours. The reaction medium is concentrated under reduced pressure (2 kPa; 40° C.) and the residue is taken up in 25 cm³ of ethyl acetate and 25 cm³ of water. The organic phase is washed with 25 cm³ of distilled water and then with 25 cm³ of saturated aqueous sodium chloride solution. After drying over magnesium sulfate, filtering and concentrating under reduced pressure (2 kPa; 40° C.), the residue obtained is purified by chromatography under an argon pressure of 50 kPa, on a column of silica gel (particle size 40–60 µm; diameter 3 cm), eluting with a dichloromethane/methanol mixture (98/2 by volume). The fractions containing the expected product are combined and then evaporated under reduced pressure (2 kPa; 40° C.); after drying (90 Pa ; 40° C.), 596 mg of N-(6,7-difluoro-1H-indazol-3-yl)butanamide are obtained in the form of a white solid melting at 191° C.

¹H NMR spectrum (300 MHz, $(CD_3)_2SO$ d6, δ in ppm): 0.97 (t, J=7.5 Hz: 3H); 1.67 (mt: 2H); 2.40 (t, J=7 Hz: 2H); 7.10 (mt: 1H); 7.63 (broad dd, J=9 and 4.5 Hz: 1H); 10.47 (broad unresolved complex: 1H); 13.35 (broad unresolved complex: 1H).

N-[6,7-Difluoro-1-[[2-(trimethylsilyl)ethoxy]methyl]-1H-indazol-3-yl]butanamide

A solution of 1.1 g of N-(6,7-difluoro-1H-indazol-3-yl)butanamide prepared above, in 180 cm³ of dimethylformamide, is added dropwise over 3 hours to 1.65 g of sodium hydride at 60% in oil, in 50 cm³ of dimethylformamide. The reaction medium is concentrated to dryness under reduced pressure and taken up in 250 cm³ of ethyl acetate and 200 cm³ of water; the organic phase is separated out after settling of the phases, washed with 150 cm³ of water, dried over magnesium sulfate, filtered and concentrated to dryness under reduced pressure (2 kPa; 50° C.). The crude product is purified by chromatography under an argon pressure of 50 kPa, on a column of silica gel (particle size 40–60 µm; diameter 6 cm), eluting with a cyclohexane/ethyl acetate mixture (80/20 by volume). The fractions containing the expected product are combined and evaporated under reduced pressure (2 kPa; 50° C.) to give 7.3 g of N-[6,7-difluoro-1-[[2-(trimethylsilyl)ethoxy]methyl]-1H-indazol-3-yl]butanamide in the form of a yellow oil.

¹H NMR spectrum (300 MHz, $(CD_3)_2SO$ d6, δ in ppm): –0.09 (s: 9H); 0.82 (t, J=8 Hz: 2H); 0.96 (t, J=7.5 Hz: 3H); 1.67 (mt: 2H); 2.41 (t, J=7 Hz: 2H); 3.56 (t, J=8 Hz: 2H); 5.66 (s: 2H); 7.22 (ddd, J=11–9 and 7 Hz: 1H); 7.69 (broad dd, J=9 and 4.5 Hz: 1H); 10.60 (unresolved complex: 1H). Mass spectrum: M=369

N-[5-Bromo-6,7-difluoro-1-[[2-(trimethylsilyl)ethoxy]methyl]-1H-indazol-3yl]butanamide 0.87 cm³ of pyridine is added to 1 g of N-[6,7-difluoro-1-[[2-(trimethylsilyl)ethoxy]methyl]-1H-indazol-3-yl]butanamide described above in 30 cm³ of chloroform, followed by addition of 0.56 cm³ of bromine, and the mixture is refluxed overnight. 50 cm³ of dichloromethane and 50 cm³ of aqueous 10% sodium thiosulfate solution are added to the reaction medium. After stirring for 10 minutes, the insoluble material is removed by filtration on a sinter funnel and the organic phase is washed with 50 cm³ of water and with 50 cm³ of saturated sodium chloride solution. The organic phase is separated out by settling of the phases, dried over magnesium sulfate, filtered and concentrated to dryness under reduced pressure (2 kPa; 45° C.). The crude product, 1.1 g, is purified by chromatography under an argon pressure of 50 kPa, on a column of silica gel (particle size 40–60 µm; diameter 3 cm), eluting with a cyclohexane/ethyl acetate mixture (90/10 by volume). The fractions containing the expected product are combined and evaporated under reduced pressure (2 kPa; 50° C.). After drying (90 Pa; 45° C.), 230 mg of N-[5-bromo-6,7-difluoro-1-[[2-(trimethylsilyl)ethoxy]methyl]-1H-indazol-3-yl]butanamide are obtained in the form of a colorless oil.

¹H NMR spectrum (300 MHz, $(CD_3)_2SO$ d6, δ in ppm): –0.08 (s: 9H); 0.82 (t, J=8 Hz: 2H); 0.96 (t, J=7.5 Hz: 3H); 1.67 (mt: 2H); 2.42 (t, J=7 Hz: 2H); 3.55 (t, J=8 Hz: 2H);

5.66 (s: 2H); 8.08 (dd, J=6 and 2 Hz : 1H); 10.72 (unresolved complex: 1H). Mass spectrum: M=447

N-[6,7-Difluoro-5-phenyl-1-[[2-(trimethylsilyl) ethoxy]methyl]-1H-indazol-3-yl]butanamide 469 mg of phenylboronic acid, 760 mg of sodium carbonate in 30 cm³ of water and 379 mg of tetrakis(triphenylphosphine)palladium are added to 1.15 g of N-[5-bromo-6,7-difluoro-1-[[2-(trimethylsilyl)ethoxy]methyl]-1H-indazol-3-yl]butanamide prepared above, in 150 cm³ of dioxane, and the mixture is refluxed for 4 hours. The reaction medium is diluted with 100 cm³ of ethyl acetate and 75 cm³ of water and is filtered through a sinter funnel packed with Celite. The organic phase is separated out after settling of the phases, washed with 75 cm³ of water and with 75 cm³ of saturated sodium chloride solution, dried over magnesium sulfate, filtered and concentrated to dryness under reduced pressure (2 kPa; 50° C.) to give 2 g of crude product in the form of a black oil. The crude product is purified by chromatography under an argon pressure of 50 kPa, on a column of silica gel (particle size 40–60 μm; diameter 3.5 cm), eluting with a cyclohexane/ethyl acetate mixture (85/15 by volume). The fractions containing the expected product are combined, evaporated under reduced pressure (2 kPa; 50° C.) and dried (90 Pa, 45° C.) to give 1.1 g of N-[6,7-difluoro-5-phenyl-1-[[2-(trimethylsilyl)ethoxy]methyl]-1H-indazol-3-yl]butanamide in the form of a yellow oil.
$^1$H NMR spectrum (300 MHz, $(CD_3)_2SO$ d6, δ in ppm): –0.05 (s: 9H); 0.84 (t, J=8 Hz: 2H); 0.95 (t, J=7.5 Hz: 3H); 1.66 (mt: 2H); 2.43 (t, J=7 Hz: 2H); 3.59 (t, J=8 Hz: 2H); 5.69 (s: 2H); from 7.40 to 7.65 (mt: 5H); 7.82 (broad d, J=7 Hz: 1H); 10.64 (unresolved complex: 1H). Mass spectrum: M=445

N-[6,7-Difluoro-5-phenyl-1-[[2-(trimethylsilyl) ethoxy]methyl]-1H-indazole-3-amine 1.1 cm³ of ethanolamine and then 1.50 g of potassium carbonate are added to 1.6 g of N-[6,7-difluoro-5-phenyl-1-[[2-(trimethylsilyl)ethoxy]methyl]-1H-indazol-3-yl]butanamide described above, in 50 cm³ of dimethylformamide, and the mixture is refluxed for one week. The reaction medium is concentrated to dryness under reduced pressure and taken up in 150 cm³ of ethyl acetate and 75 cm³ of water. The organic phase is separated out after settling of the phases and washed successively with twice 75 cm³ of water and 50 cm³ of brine. The organic phase is dried over magnesium sulfate, filtered and then concentrated to dryness under reduced pressure (2 kPa; 50° C.). The crude oil obtained is purified by chromatography under an argon pressure of 50 kPa, on a column of silica gel (particle size 40–60 μm; diameter 4 cm), eluting with a cyclohexane/ethyl acetate mixture (80/20 by volume). The fractions containing the expected product are combined and evaporated under reduced pressure (2 kPa; 50° C.). After drying (90 Pa; 45° C.), 0.32 g of 6,7-difluoro-5-phenyl-1-[[2-(trimethylsilyl)ethoxy]methyl]-1H-indazole-3-amine is obtained.

6,7-Difluoro-5-phenyl-1H-indazole-3-amine 1.1 ml of 2N HCl are added to 661 mg of 6,7-difluoro-5-phenyl-1-[[2-(trimethylsilyl)ethoxy]methyl]-1H-indazole-3-amine in 15 ml of methanol. The reaction is subjected to microwaves for 3 minutes at 140° C. After hydrolysis with saturated $KH_2PO_4$ solution and extraction with methylene chloride, the solvents are evaporated off and the residue is chromatographed on silica (methylene chloride/ethyl acetate) to give 314 mg of 6,7-difluoro-5-phenyl-1H-indazole-3-amine.

EXAMPLE 1

Piperidine-1-carboxylic acid (6,7-difluoro-5-phenyl-1H-indazol-3-yl)amide

Step 1

131 μl of pyridine and 154 μl of ethyl chloroformate are successively added to 387.8 mg of (6,7-difluoro-5-phenyl-1-[[2-(trimethylsilyl)ethoxy]methyl]-1H-indazole-3-amine compound in 8 ml of methylene chloride. After 75 minutes, the reaction is complete. After hydrolysis, extraction and evaporation, 840 mg of crude ethyl (6,7-difluoro-5-phenyl-1H-indazol-3-yl)carbamate are obtained.

Step 2

184 mg of piperidine are added to 161 mg of crude ethyl (6,7-difluoro-5-phenyl-1H-indazol-3-yl)carbamate in 2.5 ml of trifluorotoluene and the reaction is performed under microwaves for 20 minutes at 200° C. After purification by preparative LC/MS (acetonitrile/pH 9 buffer), 80 mg of piperidine-1-carboxylic acid (6,7-difluoro-5-phenyl-1-[[2-(trimethylsilyl)ethoxy]methyl]-1H-indazol-3-yl)amide are obtained.

Step 3

80 mg of piperidine-1-carboxylic acid (6,7-difluoro-5-phenyl-1-[[2-(trimethylsilyl)ethoxy]methyl]-1H-indazol-3-yl)amide in 2.5 ml of methanol are treated with 0.82 ml of 2N HCl for 1 hour at reflux. After evaporation and purification by preparative LC/MS (acetonitrile/pH 9 buffer), 11 mg of piperidine-1-carboxylic acid (6,7-difluoro-5-phenyl-1H-indazol-3-yl)amide are obtained.

Mass spectrum: retention time 3.99; 357=[M+H]$^{+1}$H NMR spectrum (300 MHz, (DMSO-d6, δ in ppm): 1.50 (m, 4H); 1.58 (m, 2H); 3.45 (m, 4H); 7.42 (m, 1H); 7.51 (m, 5H); 9.16 (s, 1H); 13.20 (bs, 1H)

EXAMPLE 2

Pyrrolidine-1-carboxylic acid (6,7-difluoro-5-phenyl-1H-indazol-3-yl)amide

Step 1

154 mg of pyrrolidine are added to 161 mg of ethyl (6,7-difluoro-5-phenyl-1H-indazol-3-yl)carbamate in 2.5 ml of trifluorotoluene, and the reaction is performed under microwaves for 20 minutes at 200° C. The product is purified on a column of silica to give 75 mg of pyrrolidine-1-carboxylic acid (6,7-difluoro-5-phenyl-1-[[2-(trimethylsilyl)ethoxy]methyl]-1H-indazol-3-yl)amide.

Step 2

75 mg of pyrrolidine-1-carboxylic acid (6,7-difluoro-5-phenyl-1-[[2-(trimethylsilyl)ethoxy]methyl]-1H-indazol-3-yl)amide in 3 ml of methanol are treated with 0.82 ml of 2N HCl for 1 hour at reflux. After evaporation and purification by preparative LC/MS (acetonitrile/pH 9 buffer), 36 mg of pyrrolidine-1-carboxylic acid (6,7-difluoro-5-phenyl-1H-indazol-3-yl)amide are obtained.

Mass spectrum: retention time 3.72 minutes; 343=[M+H]$^{+1}$H NMR spectrum (300 MHz, (DMSO-d6, δ in ppm): 1.86 (m, 4H); 3.40 (m, 4H); 7.42 (m, 1H); from 7.45 to 7.54 (m, 4H); 7.63 (bd, J=7 Hz, 1H); 8.84 (s, 1H); 13.20 (bs, 1H)

EXAMPLE 3

Performed According to Example 2, Starting with 3-(4-methylpiperazin-1-yl)propylamine, to Give 1-(6,7-difluoro-5-phenyl-1H-indazol-3-yl)-3-[3-(4-methylpiperazin-1-yl)propyl]urea $^1$H NMR spectrum (300 MHz, (DMSO-d6, δ in ppm): 1.92 (m, 2H); 2.82 (s, 3H); from 3.01 to 3.75 (m, partially masked, 12 H); 7.43 (m, 1H); from 7.47 to 7.56 (m, 4H); 7.71 (t, J=7 Hz, 1H); 8.05 (dd, J=1.5–7 Hz, 1H); 9.61 (s,1H) Mass spectrum: retention time 2.57 minutes; 429=[M+H]$^+$ The pharmaceutical compositions according to the invention are composed of a compound of formula (I) or a salt of such a compound, in the pure state or in the form of a composition in which it is combined with any other pharmaceutically compatible product, which can be inert or physiologically active. The medicaments according to the invention can be employed orally, parenterally, rectally or topically.

Use may be made, as solid compositions for oral administration, tablets, pills, powders (of hard gelatin capsules, cachets) or granules. In these compositions, the active principle according to the invention is mixed with one or more inert diluents, such as starch, cellulose, sucrose, lactose or silica, under an argon stream. These compositions can also comprise substances other than the diluents, for example one or more lubricants, such as magnesium stearate or talc, a colorant, a coating (dragees) or a glaze.

Use may be made, as liquid compositions for oral administration, of pharmaceutically acceptable solutions, suspensions, emulsions, syrups and elixirs comprising inert diluents, such as water, ethanol, glycerol, vegetable oils or liquid paraffin. These compositions can comprise substances other than the diluents, for example wetting, sweetening, thickening, flavoring or stabilizing products.

The sterile compositions for parenteral administration can preferably be solutions in aqueous or nonaqueous form, suspensions or emulsions. Use may be made, as solvent or vehicle, of water, propylene glycol, a polyethylene glycol, vegetable oils, in particular olive oil, injectable organic esters, for example ethyl oleate, or other suitable organic solvents. These compositions can also comprise adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories or rectal capsules which comprise, in addition to the active product, excipients such as cocoa butter, semisynthetic glycerides or polyethylene glycols.

The compositions for topical administration can be, for example, creams, lotions, eye drops, mouthwashes, nose drops or aerosols.

The subject matter of the invention is the aminoindazole compounds of formula (I) and their pharmaceutically acceptable salts and their use in the preparation of pharmaceutical compositions intended to prevent and treat diseases which result from an abnormal activity of kinases, such as, for example, those involved in neurodegenerative diseases, Alzheimer's disease, Parkinson's disease, frontoparietal dementia, corticobasal degeneration, Pick's disease, strokes, cranial and spinal traumas and peripheral neuropathies, obesity, metabolic diseases, type II diabetes, essential hypertension, atherosclerotic cardiovascular diseases, polycystic ovaries syndrome, syndrome X, immunodeficiency and cancer.

Mention may be made, as abnormal kinase activity, of, for example, that of P13K, AkT or GSK3beta, of CDKs, and the like.

In human therapy, the compounds according to the invention are of particular use in the treatment and/or prevention of neurodegenerative diseases, Alzheimer's disease, Parkinson's disease, frontoparietal dementia, corticobasal degeneration, Pick's disease, strokes, cranial and spinal traumas and peripheral neuropathies, obesity, metabolic diseases, type II diabetes, essential hypertension, atherosclerotic cardiovascular diseases, polycystic ovaries syndrome, syndrome X, immunodeficiency and cancer.

The doses depend on the desired effect, on the duration of the treatment and on the administration route used; they are generally between 5 mg and 1000 mg per day orally for an adult with unit doses ranging from 1 mg to 250 mg of active substance.

Generally, the doctor will determine the appropriate dosage according to the age, weight and all the other factors specific to the subject to be treated.

The following examples illustrate compositions according to the invention:

EXAMPLE A

Hard gelatin capsules, with doses of 50 mg of active product, having the following composition are prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets, with doses of 50 mg of active product, having the following composition are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerol and titanium oxide (72/3.5/24.5) q.s. for 1 coated tablet completed to | 245 mg |

EXAMPLE C

An injectable solution comprising 10 mg of active product having the following composition is prepared:

| | |
|---|---|
| Compound of formula (I) | 10 mg |
| Benzoic acid | 80 mg |
| Benzyl alcohol | 0.06 ml |
| Sodium benzoate | 80 mg |
| 95% Ethanol | 0.4 ml |
| Sodium hydroxide | 24 mg |
| Propylene glycol | 1.6 ml |
| Water | q.s. for 4 ml |

The present invention also relates to the method for the prevention and treatment of diseases in which a phosphorylation of the tau protein is involved by administration of a compound of formula (I) and its pharmaceutically acceptable salts.

What is claimed is:

1. A compound of formula (I):

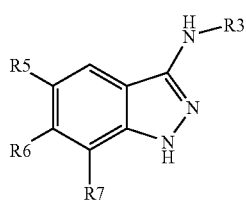

(I)

wherein
R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1, C(=NH)R1 or C(=NH)NR1 radical; these radicals optionally being substituted by 1 or more substituents chosen from halogen, CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, heterocycle, formyl, trifluoromethyl, trifluoromethylsulfanyl, trifluoromethoxy or (1–6C)alkyl;

R5, R6 and R7 are, independently of one another, chosen from the following radicals: halogen, CN, NO2, NH$_2$, OH, COOH, C(O)OR8, —O—C(O)R8, NR8R9, NHC(O)R8, C(O)NR8R9, NHC(S)R8, C(S)NR8R9, SR8, S(O)R8, SO$_2$R8, NHSO$_2$R8, SO$_2$NR8R9, —O—SO$_2$R8, —SO$_2$—O—R8, trifluoromethyl, trifluoromethoxy, (1–6C)alkyl, (1–6C)alkoxy, aryl, aryl(1–6C)alkyl, heteroaryl, heteroaryl(1–6C)alkyl, heterocycle, cycloalkyl, alkenyl, alkynyl, adamantyl or polycycloalkyl; these radicals optionally being substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;

R1, R2, R8, R9, R10 and R11 are, independently of one another, a hydrogen, (1–6C)alkyl, aryl, alkenyl, alkynyl, heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, trifluoromethyl, trifluoromethoxy;

R1 and R2 or R8 and R9 or R10 and R11 can form a 5- or 6-membered ring which may or may not have a heteroatom, such as O, S or N;

and, when R3 is a 6-membered nitrogenous heteroaryl or a thiazolyl or an imidazolyl or an oxazolyl, then at least one of the R5 and R6 groups is an aryl which is optionally substituted by 1 or more substituents selected from halogen, CN, NO$_2$, NH$_2$, OH, OR10, COOH, C(O)OR10, —O—C(O)R10, NR10R11, NHC(O)R10, C(O)NR10R11, NHC(S)R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy and (1–6C)alkyl;

its racemates, enantiomers or diastereoisomers and their mixtures, its tautomers and its pharmaceutically acceptable salts.

2. A compound according to claim 1:
wherein
R5 and R6 are chosen, independently of one another, from the following radicals: halogen, CN, NO2, NH$_2$, OH, COOH, C(O)OR8, —O—C(O)R8, NR8R9, NHC(O)R8, C(O)NR8R9, NHC(S)R8, C(S)NR8R9, SR8, S(O)R8, SO$_2$R8, NHSO$_2$R8, SO$_2$NR8R9, —O—SO$_2$R8, —SO$_2$—O—R8, trifluoromethyl, trifluoromethoxy, (1–6C)alkyl, (1–6C)alkoxy, aryl, aryl(1–6C)alkyl, heteroaryl, heteroaryl(1–6C)alkyl, heterocycle, cycloalkyl, alkenyl, alkynyl, adamantyl, polycycloalkyls; these radicals optionally being substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;

R7 is a halogen, methyl, cyclopropyl, CN, OH, methoxy, trifluoromethyl, ethylenyl, acetylenyl, trifluoromethoxy, NO$_2$, NH$_2$ or NMe2 its racemates, enantiomers or diastereoisomers and their mixtures, its tautomers and its pharmaceutically acceptable salts.

3. A compound according to claim 2:
wherein
R5 is an aryl
R6 and R7 are, independently of one another, a halogen, methyl, cyclopropyl, CN, OH, methoxy, trifluoromethyl, ethylenyl, acetylenyl, trifluoromethoxy, NO$_2$, NH$_2$ or NMe$_2$ R1 and R2 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C) alkoxy, CN, NO$_2$, NH$_2$, OH, COOH, COOalkyl, CONH$_2$, formyl, oxo, trifluoromethyl or trifluoromethoxy;

R1 and R2 can form a 5- or 6-membered ring which may or may not have a heteroatom, such as O, S or N;

its racemates, enantiomers or diastereoisomers and their mixtures, its tautomers and its pharmaceutically acceptable salts.

4. The compound according to claim 1, which is selected from the group consisting of:

- N-(bicyclo[2.2.1]hept-5-en-2-ylmethyl)-6-chloro-7-fluoro-5-phenyl-1H-indazol-3-amine;
- 6-chloro-7-fluoro-N-(3,3-dimethylbutyl)-5-phenyl-1H-indazol-3-amine;
- 6-chloro-7-fluoro-N-(3-phenylpropyl)-5-phenyl-1H-indazol-3-amine;
- 6-chloro-7-fluoro-N-(cyclopropylmethyl)-5-phenyl-1H-indazol-3-amine;
- 6-chloro-7-fluoro-N-(cyclopentylmethyl)-5-phenyl-1H-indazol-3-amine;
- 6-chloro-7-fluoro-N-[3-(methylthio)propyl]-5-phenyl-1H-indazol-3-amine;
- 6-chloro-7-fluoro-N-(phenylethyl)-5-phenyl-1H-indazol-3-amine;
- 6-chloro-7-fluoro-N-(cyclohexylmethyl)-5-phenyl-1H-indazol-3-amine;
- 6-chloro-7-fluoro-N-propyl-5-phenyl-1H-indazol-3-amine;
- 6-chloro-7-fluoro-N-(2,2,3,3,4,4,4-heptafluorobutyl)-5-phenyl-1H-indazol-3-amine hydrate;
- 6-chloro-7-fluoro-N-(4,4,4-trifluorobutyl)-5-phenyl-1H-indazol-3-amine;
- 6-chloro-7-fluoro-N-[(4-methoxyphenyl)methyl]-5-phenyl-1H-indazol-3-amine;
- 6-chloro-7-fluoro-N-(phenylmethyl)-5-phenyl-1H-indazol-3-amine;
- 6-chloro-7-fluoro-N-[(4-cyanophenyl)methyl]-5-phenyl-1H-indazol-3-amine;
- N-[(4-chlorophenyl)methyl]-6-chloro-7-fluoro-5-phenyl-1H-indazol-3-amine;
- 6-chloro-7-fluoro-N-[(3-methoxyphenyl)methyl]-5-phenyl-1H-indazol-3-amine;
- 6-chloro-7-fluoro-N-[[4-(trifluoromethoxy)phenyl]methyl]-5-phenyl-1H-indazol-3-amine;
- N-[4-[[[6-chloro-7-fluoro-5-phenyl-1H-indazol-3yl]amino]methyl]phenyl]acetamide;
- 6-chloro-7-fluoro-N-[(3,5-dichlorophenyl)methyl]-5-phenyl-1H-indazol-3-amine;
- 6-chloro-7-fluoro-5-phenyl-N-[[4-(trifluoromethyl)phenyl]methyl]-1H-indazol-3-amine;
- 6-chloro-7-fluoro-N-[(4-fluorophenyl)methyl]-5-phenyl-1H-indazol-3-amine;
- 6-chloro-7-fluoro-N-[3-(4-methylphenoxy)phenylmethyl]-5-phenyl-1H-indazol-3-amine;
- N-(2,2,3,3,4,4,4-heptafluorobutyl)-6-chloro-7-fluoro-5-phenyl-1H-indazol-3-amine;
- 6-chloro-7-fluoro-5-phenyl-N-[[3,5-bis(trifluoromethyl)phenyl]methyl]-1H-indazol-3-amine;
- 6-chloro-7-fluoro-5-phenyl-N-[[3-(trifluoromethyl)phenyl]methyl]-1H-indazol-3-amine;
- 6-chloro-7-fluoro-N-[(6-methoxy-2-naphthyl)methyl]-5-phenyl-1H-indazol-3-amine;
- 6-chloro-7-fluoro-N-[(pentafluorophenyl)methyl]-5-phenyl-1H-indazol-3-amine;
- 6-chloro-7-fluoro-N-[[4-(methylthio)phenyl]methyl]-5-phenyl-1H-indazol-3-amine;
- N-[(4-chloro-3-fluorophenyl)methyl]-6-chloro-7-fluoro-5-phenyl-1H-indazol-3-amine;
- 6-chloro-7-fluoro-5-phenyl-N-(3,3,3-trifluoropropyl)-1H-indazol-3-amine;
- 6-chloro-7-fluoro-5-phenyl-N-(3-thienylmethyl)-1H-indazol-3-amine;
- N-(bicyclo[2.2.1]hept-5-en-2-ylmethyl)-6-chloro-7-fluoro-5-phenyl-1H-indazol-3-amine;
- N-(1,1'-biphenyl-4-ylmethyl)-6-chloro-7-fluoro-5-phenyl-1H-indazol-3-amine;
- 6-chloro-7-fluoro-N-[[4-(dimethylamino)phenyl]methyl]-5-phenyl-1H-indazol-3-amine;
- N-(2,2'-bithiophen-5-ylmethyl)-6-chloro-7-fluoro-5-phenyl-1H-indazol-3-amine;
- 6-chloro-7-fluoro-5-phenyl-N-[[1-(phenylmethyl)-1H-imidazol-2-yl]methyl]-1H-indazol-3-amine;
- 6-chloro-7-fluoro-N-[[1-methyl-1H-imidazol-2-yl]methyl]-5-phenyl-1H-indazol-3-amine;
- 6-chloro-7-fluoro-N-[(l-methyl-1H-indol-3-yl)methyl]-5-phenyl-1H-indazol-3-amine;
- 6-chloro-7-fluoro-N-[(5-methyl-2-furanyl)methyl]-5-phenyl-1H-indazol-3-amine;
- 6-chloro-7-fluoro-5-phenyl-N-(1H-pyrrol-2-ylmethyl)-1H-indazol-3-amine;
- 6-chloro-7-fluoro-5-phenyl-N-[(1H-imidazol-2-yl)methyl]-1H-indazol-3-amine;
- 6-chloro-7-fluoro-5-phenyl-N-[(1H-imidazol-4-yl)methyl]-1H-indazol-3-amine;
- 6-chloro-7-fluoro-5-phenyl-N-(1H-pyrazol-3-ylmethyl)-1H-indazol-3-amine;
- 6-chloro-7-fluoro-N-[[2-methyl-1H-imidazol-4-yl]methyl]-5-phenyl-1H-indazol-3-amine;
- 6-chloro-7-fluoro-N-[(3,5-dimethyl-1-phenyl-1H-pyrazol-4-yl)methyl]-5-phenyl-1H-indazol-3-amine;
- 6-chloro-7-fluoro-5-phenyl-N-[[2-phenyl-1H-imidazol-4-yl]methyl]-1H-indazol-3-amine;
- 6-chloro-7-fluoro-N-[[5-(4-chlorophenyl)-2-furanyl]methyl]-5-phenyl-1H-indazol-3-amine;
- 6-chloro-7-fluoro-5-phenyl-N-[(1-methyl-1H-pyrrol-2-yl)methyl]-1H-indazol-3-amine;
- 4-[5-[[[6-chloro-7-fluoro-5-phenyl-1H-indazol-3-yl]amino]methyl]-2-furanyl]-benzenesulfonamide;
- 6-chloro-7-fluoro-5-phenyl-N-(3-thienylmethyl)-1H-indazol-3-amine;
- 6-chloro-7-fluoro-5-phenyl-N-[[2-phenyl-1H-imidazol-4-yl]methyl]-1H-indazol-3-amine;
- ethyl-2-[[[6-chloro-7-fluoro-5-phenyl-1H-indazol-3-yl]amino]methyl]-5-(methylthio)-1H-imidazole-4-carboxylate;
- 6-chloro-7-fluoro-5-phenyl-N-[[5-[4-(trifluoromethyl)phenyl]-2-furanyl]methyl]-1H-indazol-3-amine;
- 6-chloro-7-fluoro-5-phenyl-N-[2-(1-piperidinyl)ethyl]-1H-indazol-3-amine;
- 6-chloro-7-fluoro-N-[2-(4-morpholinyl)ethyl]-5-phenyl-1H-indazol-3-amine;
- N-(6-chloro-7-fluoro-5-phenyl-1H-indazol-3-yl)-N'-(3,5-dichlorophenyl)urea;
- N-(6-chloro-7-fluoro-5-phenyl-1H-indazol-3-yl)-N'-(2-propenyl)urea;
- N-(6-chloro-7-fluoro-5-phenyl-1H-indazol-3-yl)-N'-(phenylmethyl)urea;
- N-(6-chloro-7-fluoro-5-phenyl-1H-indazol-3-yl)-N'-(4-phenoxyphenyl)urea;
- N-(6-chloro-7-fluoro-5-phenyl-1H-indazol-3-yl)-N'-(4-methoxyphenyl)methyl]urea;
- N-(6-chloro-7-fluoro-5-phenyl-1H-indazol-3-yl)-N'-[4-(trifluoromethyl)phenyl]urea;
- N-(6-chloro-7-fluoro-5-phenyl-1H-indazol-3-yl)-N'-(4-methoxyphenyl)urea;
- N-(6-chloro-7-fluoro-5-phenyl-1H-indazol-3-yl)-N'-cyclohexylurea;
- N-(6-chloro-7-fluoro-5-phenyl-1H-indazol-3-yl)-N'-propylurea;

N-(6-chloro-7-fluoro-5-phenyl-1H-indazol-3-yl)-N'-(4-chlorophenyl)urea;
N-(6-chloro-7-fluoro-5-phenyl-1H-indazol-3-yl)-N'-(4-fluorophenyl)urea;
N-[6-chloro-7-fluoro-5-phenyl-1H-indazol-3-yl]-N'-(tricyclo[3.3.1.1$^{3,7}$]dec)-1-ylurea;
N-(6-chloro-7-fluoro-5-phenyl-1H-indazol-3-yl)-N'-(4-methylphenyl)urea;
N-(6-chloro-7-fluoro-5-phenyl-1H-indazol-3-yl)urea;
N-(6-chloro-7-methyl-5-phenyl-1H-indazol-3-yl)urea;
N-(6-chloro-7-cyano-5-phenyl-1H-indazol-3-yl)urea;
N-(6-chloro-7-cyclopropyl-5-phenyl-1H-indazol-3-yl)urea;
N-(6-chloro-7-hydroxy-5-phenyl-1H-indazol-3-yl)urea;
N-(6-chloro-7-methoxy-5-phenyl-1H-indazol-3-yl)urea;
N-(6-chloro-7-trifluoromethyl-5-phenyl-1H-indazol-3-yl)urea;
N-(6-chloro-7-trifluoromethoxy-5-phenyl-1H-indazol-3-yl)urea;
N-(6-chloro-7-nitro-5-phenyl-1H-indazol-3-yl)urea;
N-(6-chloro-7-amino-5-phenyl-1H-indazol-3-yl)urea;
N-(6-chloro-7-dimethylamino-5-phenyl-1H-indazol-3-yl)urea;
N-(6-chloro-7-ethynyl-5-phenyl-1H-indazol-3-yl)urea;
N-[6-chloro-7-fluoro-5-phenyl-1H-indazol-3-yl]-4-methyl-benzenesulfonamide;
N-[6-chloro-7-fluoro-5-phenyl-1H-indazol-3-yl]methanesulfonamide;
N-[6-chloro-7-fluoro-5-phenyl-1H-indazol-3-yl]-2-propanesulfonamide;
N-[6-chloro-7-fluoro-5-phenyl-1H-indazol-3-yl]-2,2,2-trifluoroethanesulfonamide;
N-[6-chloro-7-fluoro-5-phenyl-1H-indazol-3-yl]-2-thiophenesulfonamide;
N-[6-chloro-7-fluoro-5-phenyl-1H-indazol-3-yl]benzenesulfonamide;
N-[6-chloro-7-fluoro-5-phenyl-1H-indazol-3-yl]-4-(trifluoromethyl)benzenesulfonamide;
N-[6-chloro-7-fluoro-5-phenyl-1H-indazol-3-yl]-5-(3-isoxazolyl)-2-thiophenesulfonamide;
N-[6-chloro-7-fluoro-5-phenyl-1H-indazol-3-yl]-4-fluorobenzenesulfonamide;
N-[6-chloro-7-fluoro-5-phenyl-1H-indazol-3-yl]-4-methoxybenzenesulfonamide;
N-[6-chloro-7-fluoro-5-phenyl-1H-indazol-3-yl]benzenemethanesulfonamide;
N-[6-chloro-7-fluoro-5-phenyl-1H-indazol-3-yl]-1-methyl-1H-imidazole-4-sulfonamide;
N-[6-chloro-7-fluoro-5-phenyl-1H-indazol-3-yl]-4-(1,1-dimethylethyl)benzenesulfonamide;
N-[4-[[(6-chloro-7-fluoro-5-phenyl-1H-indazol-3-yl)amino]sulfonyl]phenyl]-acetamide;
N-[6-chloro-7-fluoro-5-phenyl-1H-indazol-3-yl]-4-methylbenzenemethanesulfonamide;
6-chloro-7-fluoro-N-(pentafluorophenyl)-5-phenyl-1H-indazol-3-amine;
6-chloro-7-fluoro-N-(3,4-difluorophenyl)-5-phenyl-1H-indazol-3-amine;
6-chloro-7-fluoro-5-phenyl-N-(2,3,5,6-tetrafluorophenyl)-1H-indazol-3-amine;
6-chloro-7-fluoro-5-phenyl-N-(2,4,6-trifluorophenyl)-1H-indazol-3-amine;
6-chloro-7-fluoro-N-(4-fluorophenyl)-5-phenyl-1H-indazol-3-amine;
6-chloro-7-fluoro-N-[3-(trifluoromethyl)phenyl]-5-phenyl-1H-indazol-3-amine;
6-chloro-7-fluoro-N-[4-(trifluoromethyl)phenyl]-5-phenyl-1H-indazol-3-amine;
6-chloro-7-fluoro-N-[3-fluoro-5-(trifluoromethyl)phenyl]-5-phenyl-1H-indazol-3-amine;
6-chloro-7-fluoro-N-(4-nitrophenyl)-5-phenyl-1H-indazol-3-amine;
6-chloro-7-fluoro-N-(3-nitrophenyl)-5-phenyl-1H-indazol-3-amine;
6-chloro-7-fluoro-N-(3-methoxyphenyl)-5-phenyl-1H-indazol-3-amine;
6-chloro-7-fluoro-N-(4-methoxyphenyl)-5-phenyl-1H-indazol-3-amine;
6-chloro-7-fluoro-N,5-diphenyl-1H-indazol-3-amine;
6-chloro-7-fluoro-N-(1-pyridinyl)-5-phenyl-1H-indazol-3-amine;
6-chloro-7-fluoro-N-(2-pyridinyl)-5-phenyl-1H-indazol-3-amine;
N-butyl-6-chloro-7-fluoro-5-phenyl-1H-indazol-3-amine;
N-(6-chloro-7-fluoro-5-phenyl-1H-indazol-3-yl)-N'-phenylurea; and
N-(6-chloro-7-fluoro-5-phenyl-1H-indazol-3-yl)-3-methoxybenzenesulfonamide;

their racemates, enantiomers or diastereoisomers and their mixtures, their tautomers and their pharmaceutically acceptable salts.

5. The compound according to claim 1, which is selected from:

Piperidine-1-carboxylic acid (6,7-difluoro-5-phenyl-1H-indazol-3-yl)amide;
Pyrrolidine-1-carboxylic acid (6,7-difluoro-5-phenyl-1H-indazol-3-yl)amide; and
1-(6,7-Difluoro-5-phenyl-1H-indazol-3-yl)-3-[3-(4-methylpiperazin-1-yl)propyl]urea;

its tautomers, and their pharmaceutically acceptable salts.

6. A pharmaceutical composition, which comprises, in a pharmaceutically acceptable medium, a compound according to claim 1.

7. A pharmaceutical composition, which comprises, in a pharmaceutically acceptable medium, a compound accoding to claim 2.

8. A pharmaceutical composition, which comprises, in a pharmaceutically acceptable medium, a compound accoding to claim 3.

* * * * *